United States Patent
Mortier et al.

(10) Patent No.: US 10,858,452 B2
(45) Date of Patent: Dec. 8, 2020

(54) SPECIFIC INTERLEUKIN-15 (IL-15) ANTAGONIST POLYPEPTIDE AND USES THEREOF FOR THE TREATMENT OF INFLAMMATORY AND AUTO-IMMUNE DISEASES

(71) Applicants: INSERM (INSTITUT NATIONAL DE LA SANTE ET DE LA RECHERCHE MEDICALE), Paris (FR); UNIVERISTE DE NANTES, Nantes (FR); UNIVERSITE D'ANGERS, Paris (FR); CENTRE NATIONAL DE LA RECHERCHE SCIENTIFIQUE (CNRS), Paris (FR); CENTRE HOSPITALIER UNIVERSITAIRE DE NANTES, Nantes (FR)

(72) Inventors: Erwan Mortier, Nantes (FR); Dihia Meghnem, Nantes (FR); Sebastien Morisseau, Nantes (FR); Yannick Jacques, Nantes (FR)

(73) Assignees: Insitut National de la Sante et de la Recherche Medicale (INSERM), Paris (FR); Universite de Nantes, Nantes (FR); Universite d'Angers, Paris (FR); Centre National de la Recherche Scientifique, Paris (FR); Centre Hospitalier Universitaire de Nantes, Nantes (FR)

( * ) Notice: Subject to any disclaimer, the term of this patent is extended or adjusted under 35 U.S.C. 154(b) by 8 days.

(21) Appl. No.: 15/754,664

(22) PCT Filed: Sep. 15, 2016

(86) PCT No.: PCT/EP2016/071759
§ 371 (c)(1),
(2) Date: Feb. 23, 2018

(87) PCT Pub. No.: WO2017/046200
PCT Pub. Date: Mar. 23, 2017

(65) Prior Publication Data
US 2018/0258174 A1   Sep. 13, 2018

(30) Foreign Application Priority Data
Sep. 16, 2015   (EP) .................................... 15306418

(51) Int. Cl.
| C07K 19/00 | (2006.01) |
| C07K 14/54 | (2006.01) |
| C07K 14/715 | (2006.01) |
| A61P 37/06 | (2006.01) |
| A61K 38/20 | (2006.01) |
| C12N 15/62 | (2006.01) |
| A61K 39/395 | (2006.01) |
| C07K 16/28 | (2006.01) |
| A61K 38/17 | (2006.01) |

(52) U.S. Cl.
CPC ........ *C07K 19/00* (2013.01); *A61K 39/39533* (2013.01); *C07K 14/5443* (2013.01); *C07K 14/7155* (2013.01); *C07K 16/2866* (2013.01); *C12N 15/62* (2013.01); *A61K 38/1774* (2013.01); *A61K 38/1793* (2013.01); *A61K 38/2086* (2013.01); *A61P 37/06* (2018.01); *C07K 2317/52* (2013.01); *C07K 2317/76* (2013.01); *C07K 2319/01* (2013.01)

(58) Field of Classification Search
None
See application file for complete search history.

(56) References Cited

U.S. PATENT DOCUMENTS

2016/0318986 A1* 11/2016 Morisseau ......... A61K 38/2086

FOREIGN PATENT DOCUMENTS

| EP | 2 915 569 A1 | 9/2015 |
| WO | 2006/020849 A2 | 2/2006 |
| WO | 2007/046006 A2 | 4/2007 |
| WO | 2008/143794 A1 | 11/2008 |
| WO | 2014/170032 A1 | 10/2014 |
| WO | 2015/018528 A1 | 2/2015 |
| WO | 2015/018529 A1 | 2/2015 |

OTHER PUBLICATIONS

Bowie et al. (Science, 1990, 247:1306-1310) (Year: 1990).*
Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000, 10:398-400) (Year: 2000).*
Kim et al., "Targeting the IL-15 Receptor with an Antagonist IL-15 Mutant/Fcgamma2a Protein Blocks Delayed-Type Hypersensitivity", The Journal of Immunology, 1998, 160: 5742-5748.
Mortier et al., "Soluble Interleukin-15 Receptor alpha (IL-15Ralpha)-sushi as a Selective and Potent Agonist of IL-15 Action through IL-15Rbeta/gamma", The Journal of Biological Chemistry, vol. 281, No. 3, pp. 1612-1619, Jan. 20, 2006.

* cited by examiner

*Primary Examiner* — Brian Gangle
*Assistant Examiner* — Andrea K McCollum
(74) *Attorney, Agent, or Firm* — W & C IP

(57) ABSTRACT

The present invention relates to specific interleukin-15 (IL-15) antagonist polypeptides and uses thereof for the treatment of inflammatory and auto-immune diseases. In particular, the present invention relates to a specific interleukin-15 (IL-15) antagonist polypeptide comprising i) a IL15-Ralpha sushi-containing polypeptide comprising an amino acid sequence having at least 80% of identity with the amino acid sequence of SEQ ID NO:1 ii) a linker and iii) an IL-polypeptide comprising the amino acid sequence having at least at least 80% of identity with the amino acid sequence of SEQ ID NO:4 provided that the glutamine (Q) residue at position 108 is mutated.

4 Claims, 26 Drawing Sheets

Specification includes a Sequence Listing.

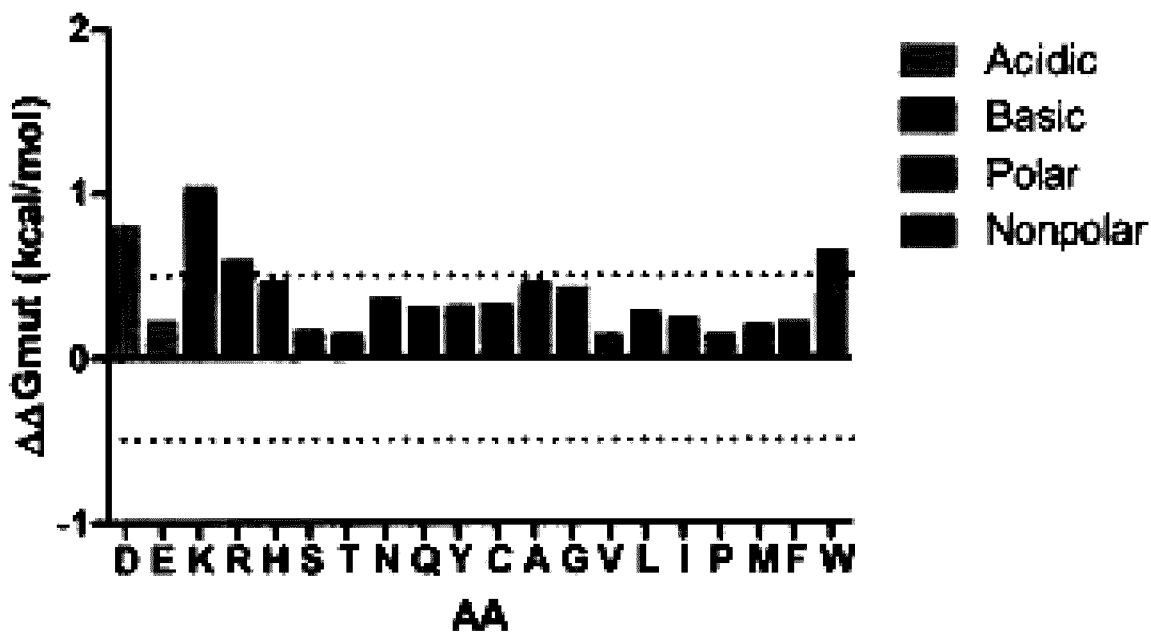
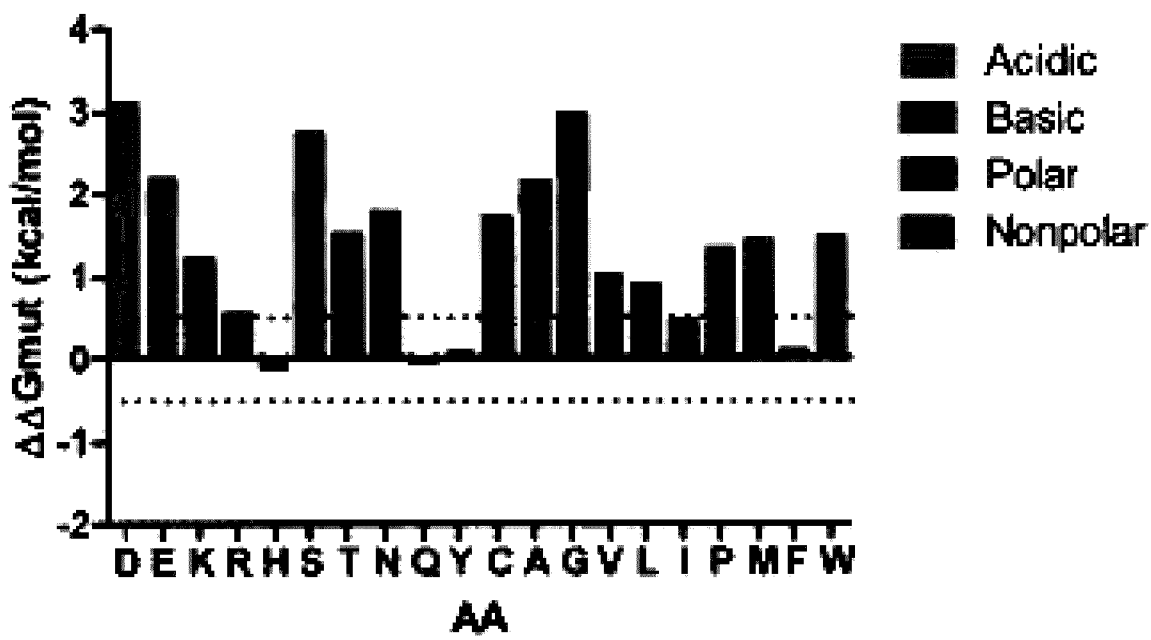
Figure 10

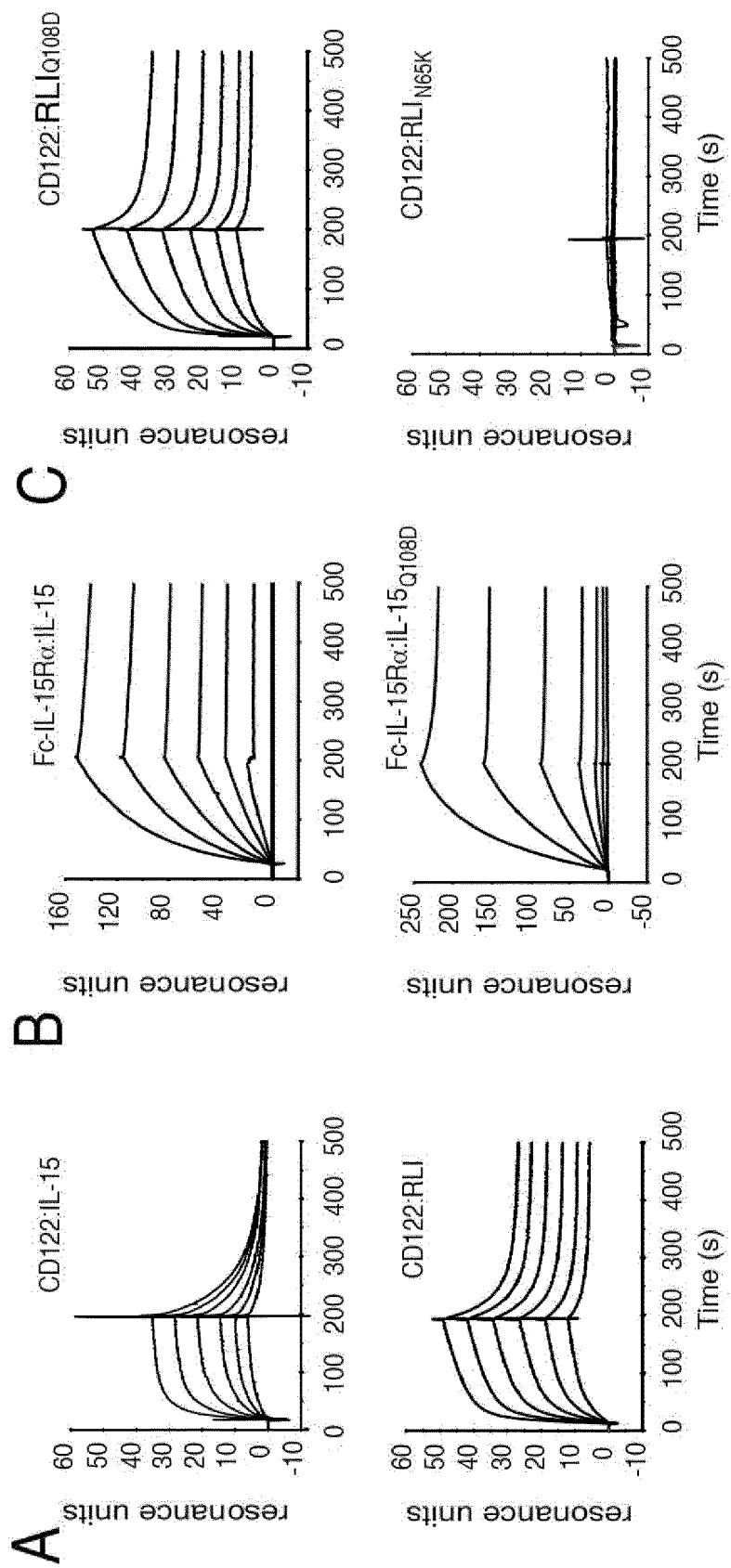
Figures 11A-C

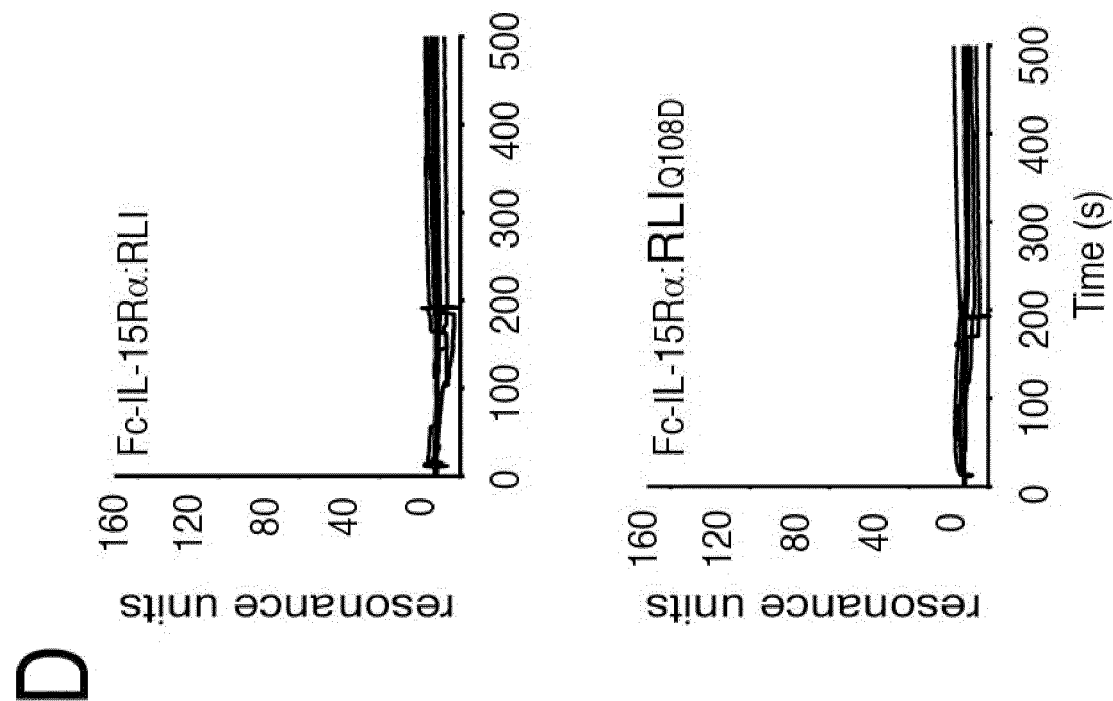
Figures 11D-E

Figure 13B:
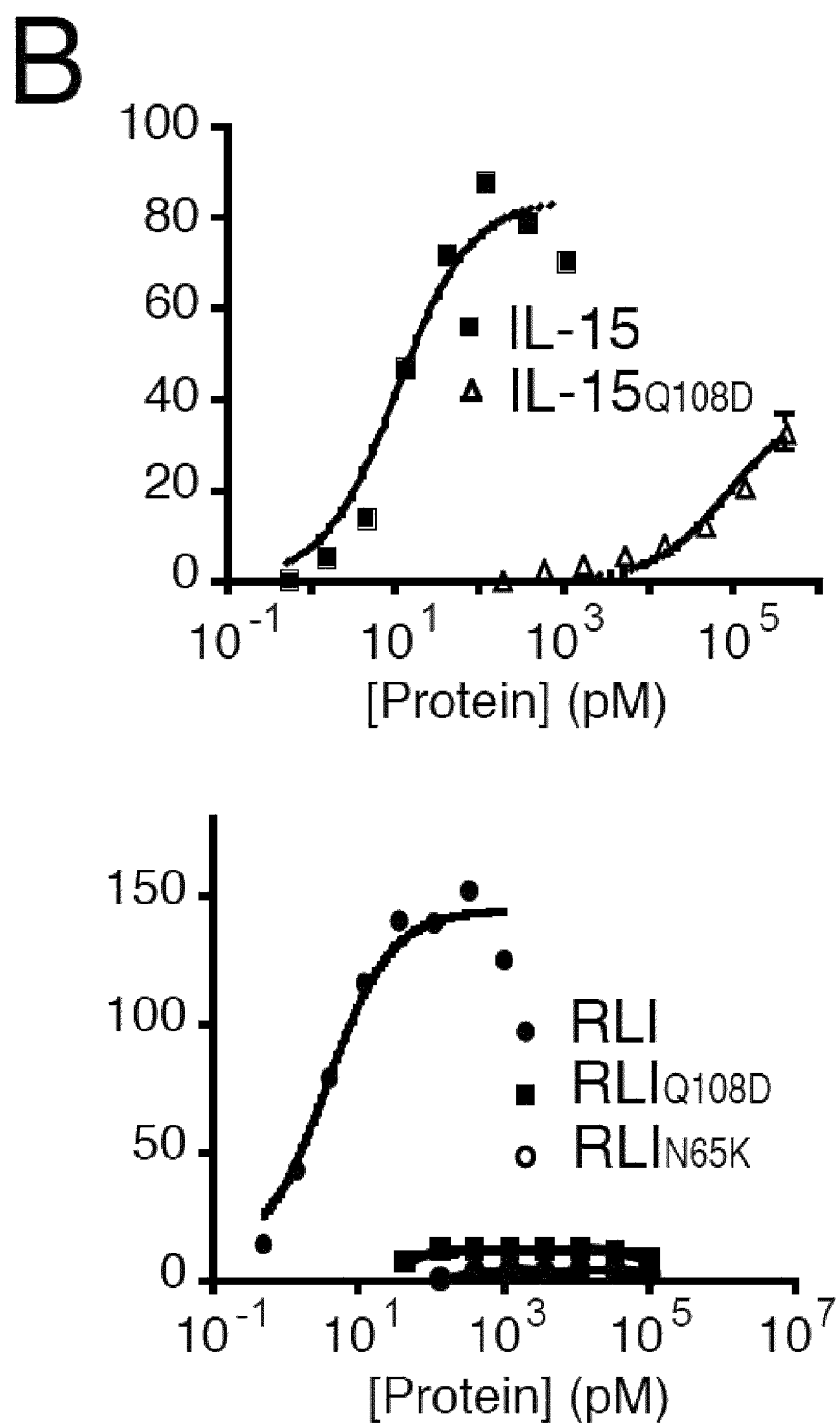

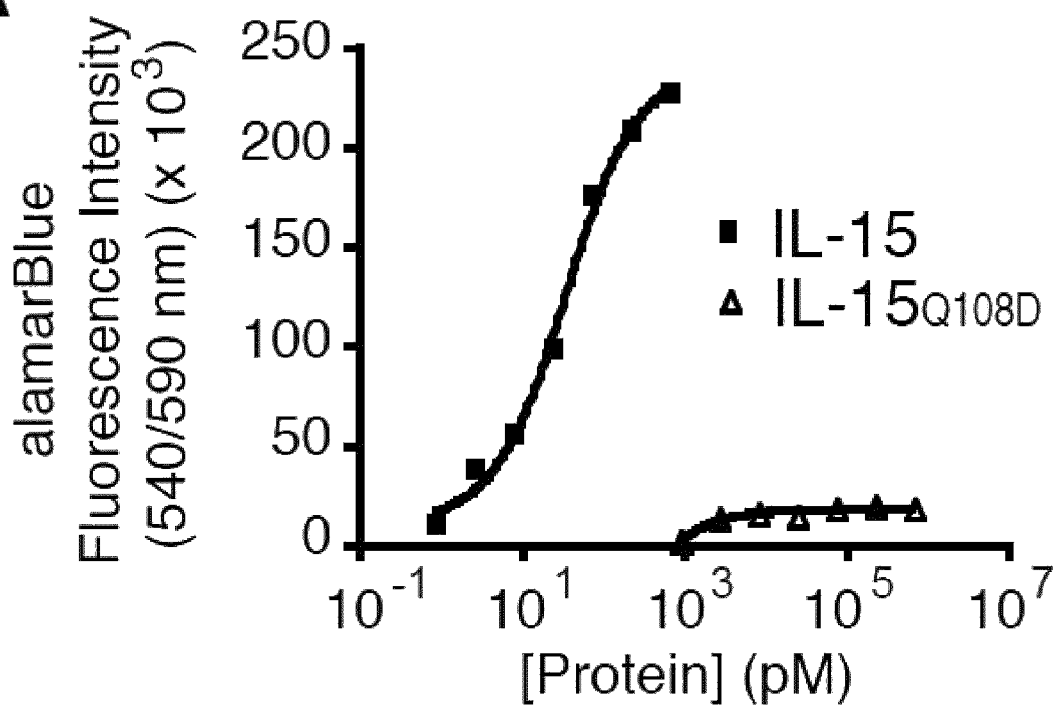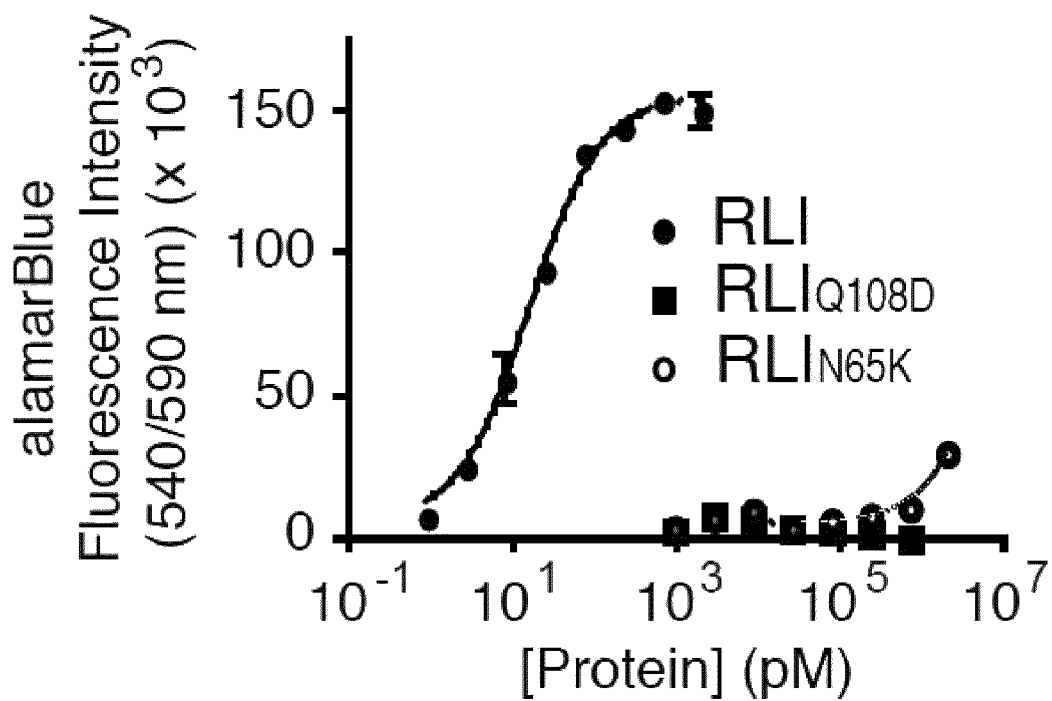
Figure 13A

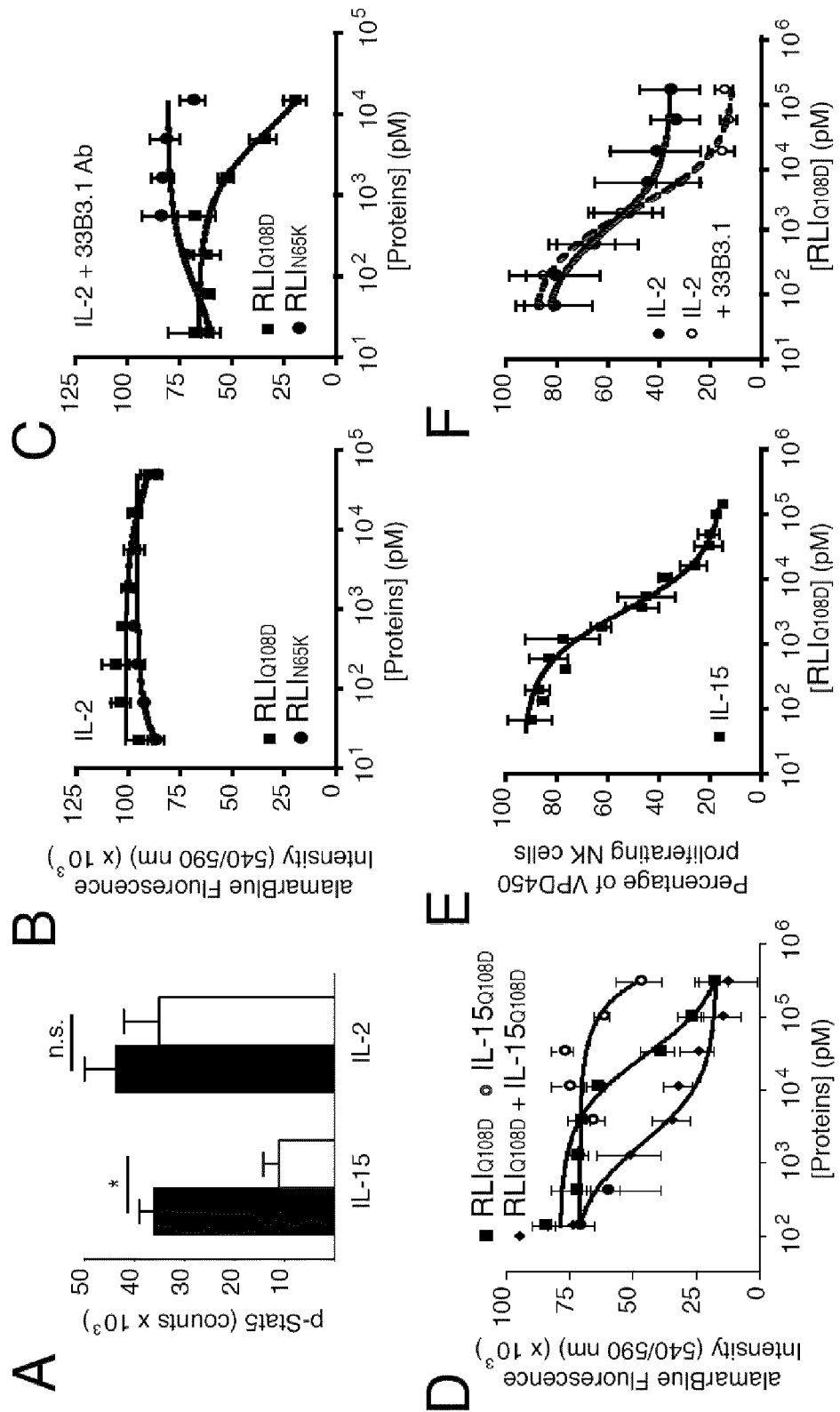
Figures 18A-F

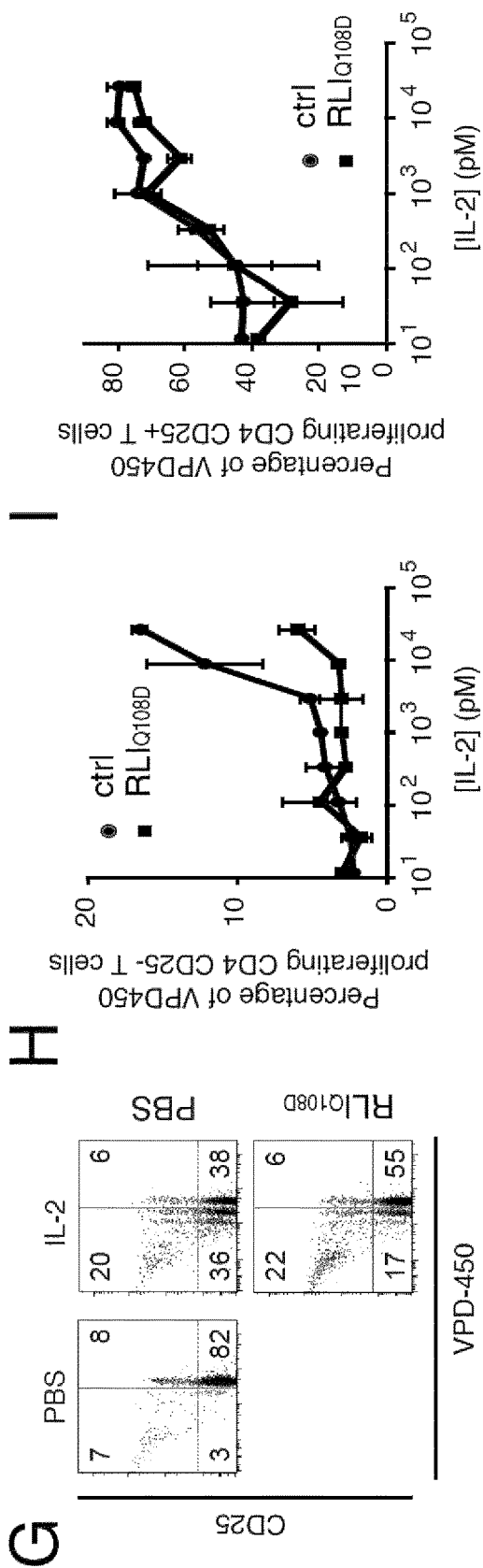
Figures 18G-I

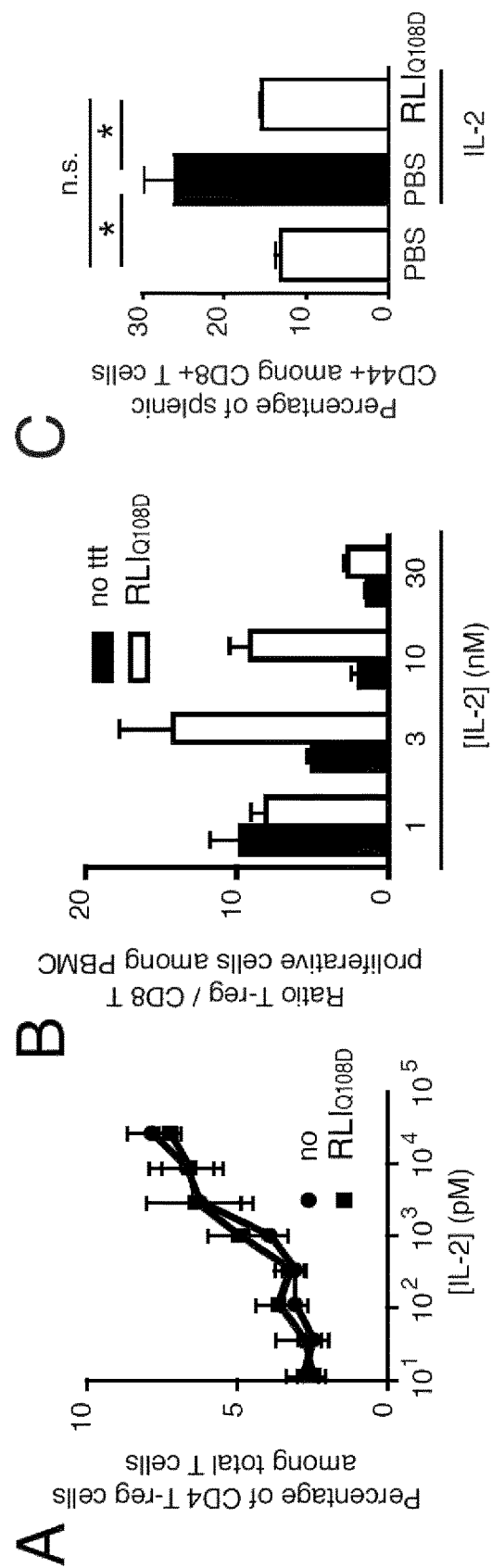
Figures 20A-C

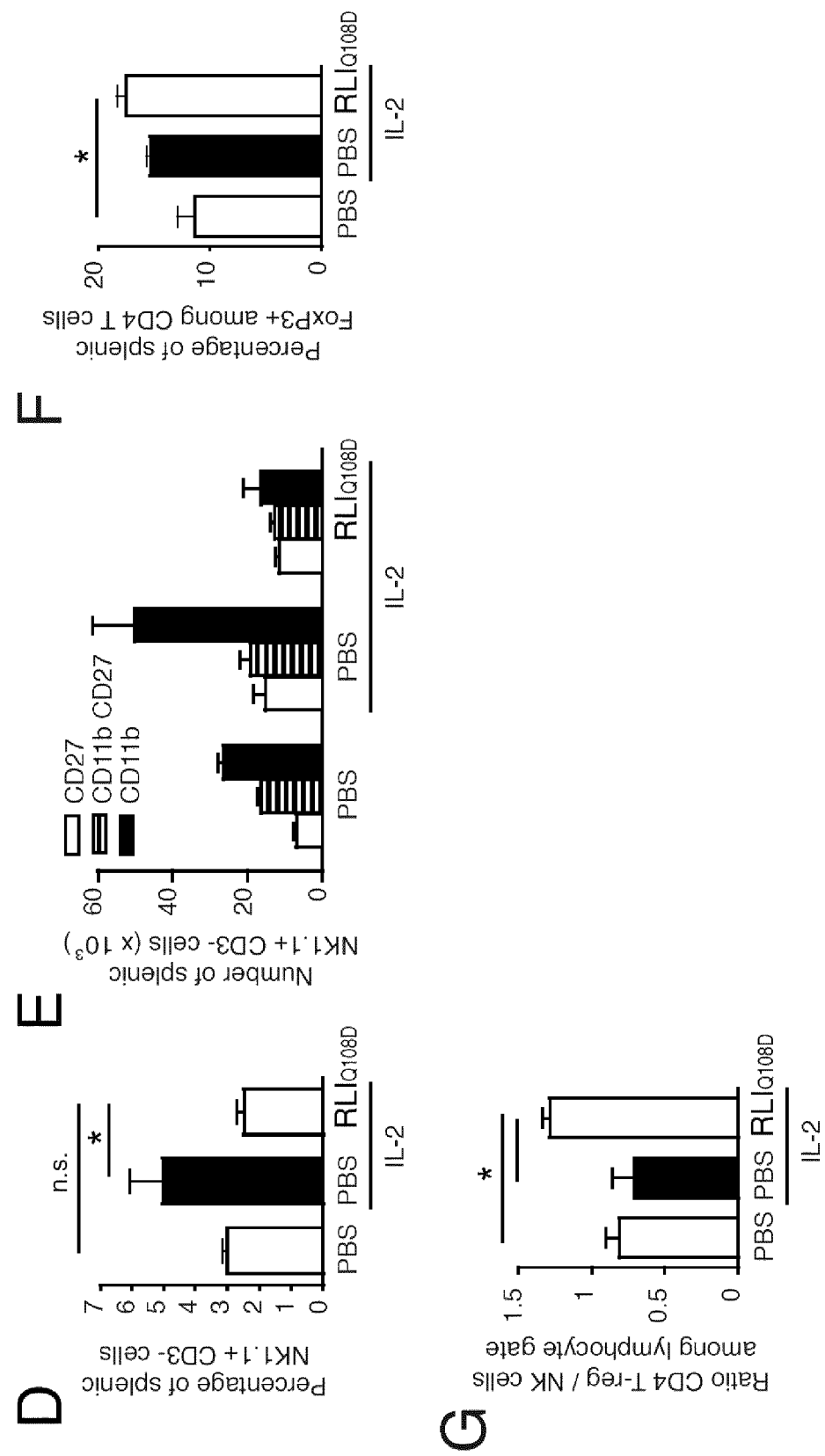
Figures 20D-G

SEQUENCE LISTING

<160> NUMBER OF SEQ ID NOS: 6

<210> SEQ ID NO 1
<211> LENGTH: 77
<212> TYPE: PRT
<213> ORGANISM: Artificial Sequence
<220> FEATURE:
<223> OTHER INFORMATION: Synthetic IL15-Ralpha sushi-containing
      polypeptide

<400> SEQUENCE: 1

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly

```
                    20                  25                  30

Phe Lys Arg Lys Ala Gly Thr Ser Ser Leu Thr Glu Cys Val Leu Asn
                35                  40                  45

Lys Ala Thr Asn Val Ala His Trp Thr Thr Pro Ser Leu Lys Cys Ile
            50                  55                  60

Arg Asp Pro Ala Leu Val His Gln Arg Pro Ala Pro Pro
65                  70                  75
```

<210> SEQ ID NO 2
<211> LENGTH: 20
<212> TYPE: PRT
<213> ORGANISM: Artificial Sequence
<220> FEATURE:
<223> OTHER INFORMATION: Synthetic linker

<400> SEQUENCE: 2

```
Ser Gly Gly Ser Gly Gly Gly Gly Ser Gly Gly Ser Gly Gly Gly
1               5                   10                  15

Gly Ser Leu Gln
            20
```

<210> SEQ ID NO 3
<211> LENGTH: 20
<212> TYPE: PRT
<213> ORGANISM: Artificial Sequence
<220> FEATURE:
<223> OTHER INFORMATION: Synthetic linker

<400> SEQUENCE: 3

```
Ser Gly Gly Ser Gly Gly Gly Gly Ser Gly Gly Ser Gly Gly Gly
1               5                   10                  15

Gly Ser Gly Gly
            20
```

<210> SEQ ID NO 4
<211> LENGTH: 114
<212> TYPE: PRT
<213> ORGANISM: Homo sapiens

<400> SEQUENCE: 4

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
            50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser
```

<210> SEQ ID NO 5
<211> LENGTH: 211
<212> TYPE: PRT
<213> ORGANISM: Artificial Sequence

```
<220> FEATURE:
<223> OTHER INFORMATION: Synthetic specific IL-15 antagonist polypeptide

<400> SEQUENCE: 5

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Gly Gly
65                  70                  75                  80

Ser Gly Gly Gly Gly Ser Gly Gly Gly Ser Gly Gly Gly Gly Ser Gly
                85                  90                  95

Gly Asn Trp Val Asn Val Ile Ser Asp Leu Lys Lys Ile Glu Asp Leu
            100                 105                 110

Ile Gln Ser Met His Ile Asp Ala Thr Leu Tyr Thr Glu Ser Asp Val
        115                 120                 125

His Pro Ser Cys Lys Val Thr Ala Met Lys Cys Phe Leu Leu Glu Leu
    130                 135                 140

Gln Val Ile Ser Leu Glu Ser Gly Asp Ala Ser Ile His Asp Thr Val
145                 150                 155                 160

Glu Asn Leu Ile Ile Leu Ala Asn Asn Ser Leu Ser Ser Asn Gly Asn
                165                 170                 175

Val Thr Glu Ser Gly Cys Lys Glu Cys Glu Glu Leu Glu Glu Lys Asn
            180                 185                 190

Ile Lys Glu Phe Leu Gln Ser Phe Val His Ile Val Asp Met Phe Ile
        195                 200                 205

Asn Thr Ser
    210

<210> SEQ ID NO 6
<211> LENGTH: 211
<212> TYPE: PRT
<213> ORGANISM: Artificial Sequence
<220> FEATURE:
<223> OTHER INFORMATION: Synthetic specific IL-15 antagonist polypeptide

<400> SEQUENCE: 6

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Gly Gly
65                  70                  75                  80

Ser Gly Gly Gly Gly Ser Gly Gly Gly Ser Gly Gly Gly Gly Ser Gly
                85                  90                  95

Gly Asn Trp Val Asn Val Ile Ser Asp Leu Lys Lys Ile Glu Asp Leu
            100                 105                 110

Ile Gln Ser Met His Ile Asp Ala Thr Leu Tyr Thr Glu Ser Asp Val
```

```
            115                 120                 125
His Pro Ser Cys Lys Val Thr Ala Met Lys Cys Phe Leu Leu Glu Leu
        130                 135                 140

Gln Val Ile Ser Leu Glu Ser Gly Asp Ala Ser Ile His Asp Thr Val
145                 150                 155                 160

Glu Asn Leu Ile Ile Leu Ala Asn Asn Ser Leu Ser Ser Asn Gly Asn
                165                 170                 175

Val Thr Glu Ser Gly Cys Lys Glu Cys Glu Glu Leu Glu Glu Lys Asn
            180                 185                 190

Ile Lys Glu Phe Leu Asp Ser Phe Val His Ile Val Asp Met Phe Ile
        195                 200                 205

Asn Thr Ser
        210
```

SPECIFIC INTERLEUKIN-15 (IL-15) ANTAGONIST POLYPEPTIDE AND USES THEREOF FOR THE TREATMENT OF INFLAMMATORY AND AUTO-IMMUNE DISEASES

FIELD OF THE INVENTION

The present invention relates to specific interleukin-15 (IL-15) antagonist polypeptides and uses thereof for the treatment of inflammatory and auto-immune diseases.

BACKGROUND OF THE INVENTION

IL-2 and IL-15 belong to a family of γc cytokines (IL-2, 4, 7, 9, 15, and 21) which are key regulators of lymphocyte homeostasis and function. They have the potential to promote lymphocyte proliferation and survival and thus overall enhance dominantly adaptive immune responses. Both cytokines share two receptor subunits, CD122 and CD132, β, and common γc chains, respectively. IL-2 exerts its pleiotropic activities through binding to either a dimeric receptor composed of CD122 and CD132 or a trimeric receptor composed of CD25, CD122 and CD132. For instance a complex of CD25, CD122 and CD132 binds IL-2 with high affinity (Ka 1011 M-1) and is present on activated T cells and T regulatory cells (Treg; CD3+CD4+CD25+Foxp3+). CD25 is constitutively expressed at high levels in Treg cells, enabling them to utilize very low background levels of IL-2. In contrast to IL-2, IL-15 is membrane-associated cytokine acting through cell-cell contact. The dominant mechanism of IL-15 signaling in vivo is trans-presentation of IL-15 by IL-15Rα (CD215) to a heterodimeric CD122/CD132 receptor. Unlike CD25, IL-15Rα binds IL-15 with a very high affinity (Ka 1011 M-1) that is not further increased in the presence of the complete IL-15 receptor, i.e., IL-15 has 100-fold higher affinity to IL-15Rα than IL-2 to CD25. IL-15Rα is expressed on T cells, NK cells, NKT cells, B cells, DCs, monocytes and macrophages, and in thymic and BM stromal cell lines. IL-2 and IL-15 shares many functions in both the adaptive and innate immune system, because both cytokines signal through the same CD122/CD132 receptor heterodimer. Both cytokines play pivotal roles in innate and adaptative immunity. Whereas initial in vitro experiments have shown a large functional overlap in the effects of the two cytokines (induction of the proliferation and cytotoxicity of activated lymphocytes and NK cells, co-stimulation of B cell proliferation and immunoglobulin synthesis, and chemoattraction of T cells), additional experiments have indicated that they can exert complementary or even contrasting actions in vivo. Whereas IL-2 or IL-2Rα knock-out in mice was associated with autoimmune phenotypes with increased populations of activated T and B cells, IL-15 and IL-15Rα knock-out resulted in specific defects in NK, NK-T, intraepithelial lymphocytes, and memory CD8 T cells. Furthermore, IL-2 promotes peripheral tolerance by inducing activation-induced cell death. IL-2 is indeed critical to the development and function of Treg cells, whereas IL-15 inhibits IL-2-mediated activation-induced cell death, and, unlike IL-2, IL-15 is a survival factor for CD8 memory T cells. In line with these observations, it has been suggested that the major role of IL-2 is to limit continuous expansion of activated T cells, whereas IL-15 is critical for initiation of T cell division and survival of memory T cells. High levels of IL-15 expression have been associated to the pathogenesis of autoimmune and inflammatory diseases, like in Crohn's disease, psoriasis, leukemias, rheumatoid arthritis (RA) and graft rejection. Accordingly modulators of IL-15 represent a great interest in the therapeutic field. Fusion proteins (RLI and ILR), in which IL-15 and IL-15R alpha-sushi are attached by a flexible linker were described as potent adjuvants for the expansion of lymphocyte subsets (Mortier E. et al. J Biol Chem. 2006 Jan. 20; 281(3):1612-9 and WO2007046006). IL-15 antagonists could be a potential therapeutic to treat inflammatory diseases and several IL-15 antagonists have been described in the prior art. For example Ferrari-Lacraz S. et al. described an IL-15 antagonist consisting of an IL-15 mutant fused to a Fc domain of an immunoglobulin and demonstrated that said antagonist could be useful for the treatment of rheumatoid arthritis (Ferrari-Lacraz S. et al. J Immunol. 2004 Nov. 1; 173(9): 5818-26.). However IL-15 antagonists described in the prior art also potentially antagonize the IL-2 signalling pathway and could thus be associated with adverse side effects (e.g. on tolerance) when they are injected in vivo.

SUMMARY OF THE INVENTION

The present invention relates to specific interleukin-15 (IL-15) antagonist polypeptides and uses thereof for the treatment of inflammatory and auto-immune diseases. In particular, the present invention is defined by the claims.

DETAILED DESCRIPTION OF THE INVENTION

The inventors surprisingly show that the RLI fusion protein described in Mortier E. et al. J Biol Chem. 2006 Jan. 20; 281(3):1612-9 and WO2007046006 wherein at least one glutamine (Q) residue at position 101 or 108 is mutated acts as an IL-15 antagonist but does not antagonize the interleukin-2 signalling pathway. This polypeptide is the first specific IL-15 antagonist targeting the common IL-2Rb/g receptor and thus offers huge advantages over the IL-15 antagonists described in the prior art since it can inhibit the proliferation of NK cells mediated by IL-15 without affecting the homeostasis of the T regulatory cells (Treg cells) that depends from the IL-2 signalling pathway.

Accordingly, the present invention relates to a specific interleukin-15 (IL-15) antagonist polypeptide comprising i) a IL15-Ralpha sushi-containing polypeptide comprising an amino acid sequence having at least 80% of identity with the amino acid sequence of SEQ ID NO:1 ii) a linker and iii) an IL-15 polypeptide comprising the amino acid sequence having at least at least 80% of identity with the amino acid sequence of SEQ ID NO:4 provided that the glutamine (Q) residue at position 108 is mutated.

As used herein, the expression "specific interleukin-15 (IL-15) antagonist polypeptide" refers to a polypeptide that is capable of inhibiting the IL-15 signalling pathway without antagonizing the IL-2 signalling pathway.

According to the invention a first amino acid sequence having at least 80% of identity with a second amino acid sequence means that the first sequence has 80; 81; 82; 83; 84; 85; 86; 87; 88; 89; 90; 91; 92; 93; 94; 95; 96; 97; 98; 99 or 100% of identity with the second amino acid sequence.

Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci.

U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

According to the invention, the IL15-Ralpha sushi-containing polypeptide, the linker and the IL-15 polypeptide are fused in frame wherein the C-terminal end of the IL15-Ralpha sushi-containing polypeptide is fused to the N-terminal end of the linker and the C-terminal end of the linker is fused to the N-terminal end of the IL-15 polypeptide.

As used herein, the term "linker" has its general meaning in the art and refers to an amino acid sequence of a length sufficient to ensure that the proteins form proper secondary and tertiary structures.

In some embodiments, the linker is a peptidic linker which comprises at least one, but less than 30 amino acids e.g., a peptidic linker of 2-30 amino acids, preferably of 10-30 amino acids, more preferably of 15-30 amino acids, still more preferably of 19-27 amino acids, most preferably of 20-26 amino acids. In some embodiments, the linker has 2; 3; 4; 5; 6; 7; 8; 9; 10; 11; 12; 13; 14; 15; 16; 17; 18; 19; 20; 21; 22; 23; 24; 25; 26; 27; 28; 29; 30 amino acid residues. Typically, linkers are those which allow the compound to adopt a proper conformation (i.e., a conformation allowing a proper signal transducing activity through the IL-15Rbeta/gamma signalling pathway). The most suitable linker sequences (1) will adopt a flexible extended conformation, (2) will not exhibit a propensity for developing ordered secondary structure which could interact with the functional domains of fusion proteins, and (3) will have minimal hydrophobic or charged character which could promote interaction with the functional protein domains. Typical surface amino acids in flexible protein regions include Gly, Asn and Ser (i.e., G, N or S). Virtually any permutation of amino acid sequences containing Gly, Asn and Ser would be expected to satisfy the above criteria for a linker sequence. Other near neutral amino acids, such as Thr, Ala, Leu, Gln (i.e., T, A, L, Q) may also be used in the linker sequence. The length of the linker sequence may vary without significantly affecting the biological activity of the fusion protein. If used for therapeutical purposes, the linker is preferably non-immunogenic. Exemplary linker sequences are described in U.S. Pat. Nos. 5,073,627 and 5,108,910.

In some embodiments, the linker of the present invention consists of the amino acid sequence of SEQ ID NO:2 or SEQ ID NO:3.

As used herein, the term mutation has its general meaning in the art and refers to a substitution, deletion or insertion. The term "substitution" means that a specific amino acid residue at a specific position is removed and another amino acid residue is inserted into the same position. The term "deletion" means that a specific amino acid residue is removed. The term "insertion" means that one or more amino acid residues are inserted before or after a specific amino acid residue, more specifically, that one or more, preferably one or several, amino acid residues are bound to an a.-carboxyl group or an a,-amino group of the specific amino acid residue.

In some embodiments, the glutamine (Q) residue at position 108 is substituted by an amino acid residue selected from the group consisting of aspartic acid (D), glutamic acid (E), lysine (K), serine (S), threonine (T), asparagine (N), cysteine (C), alanine (A), glycine (G), valine (V), leucine (L), proline (P), methionine (M) and tryptophan (W). In some embodiments, the glutamine (Q) residue at position 108 is substituted by an aspartic acid (D) residue.

In some embodiments, the glutamine (Q) residue at position 101 in the IL-15 polypeptide is also mutated. In some embodiments, the glutamine (Q) residue at position 101 is substituted by an amino acid residue selected from the group consisting of aspartic acid (D) residue, lysine (K), and tryptophan (W). In some embodiments, the glutamine (Q) residue at position 101 is substituted by an aspartic acid (D) residue.

In some embodiments, both glutamine (Q) residues at position 101 and 108 are substituted. In some embodiments, both glutamine (Q) residues at position 101 and 108 are substituted by an aspartic acid (D) residue.

In some embodiments, the specific interleukin-15 (IL-15) antagonist polypeptide of the present invention comprises an amino acid sequence having at least 80% of identity with the amino acid sequence of SEQ ID NO:5 or SEQ ID NO:6. In some embodiments, the specific interleukin-15 (IL-15) antagonist polypeptide of the present invention consists of SEQ ID NO:5 or SEQ ID NO:6.

In some embodiments, the specific interleukin-15 (IL-15) antagonist polypeptide of the present invention is fused to an immunoglobulin domain so as to form an immunoadhesin. As used herein, the term "immunoadhesin" designates antibody-like molecules which combine the binding specificity of the specific interleukin-15 (IL-15) antagonist polypeptide of the present invention with the effector functions of immunoglobulin constant domains. In some embodiments, the immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM. In some embodiments, the immunoglobulin sequence is an immunoglobulin constant domain (Fc region). Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. The artisan skilled in the art can easily select the most appropriate Fc domain (Chan A C, Carter P J. Therapeutic antibodies for autoimmunity and inflammation. Nat Rev Immunol. 2010 May; 10(5):301-16. doi: 10.1038/nri2761. Review.). In some embodiments, the Fc region includes or not a mutation that inhibits complement fixation and/or Fc receptor binding (Zheng et al, Transplantation. 2006 Jan. 15; 81(1):109-16). In some embodiments, the Fc region is a native sequence Fc region. In some embodiments, the Fc region is a variant Fc region. In some embodiments, the Fc region is a functional Fc region. As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. In some embodiments, the adhesion portion and the immunoglobulin sequence portion of the immunoadhesin are linked by a minimal linker.

According to the invention, the specific interleukin-15 (IL-15) antagonist polypeptide of the present invention is produced by conventional automated peptide synthesis methods or by recombinant expression. General principles for designing and making proteins are well known to those of skill in the art. The specific interleukin-15 (IL-15) antagonist polypeptide of the present invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The specific interleukin-15 (IL-15) antagonist polypeptide of the present invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art. As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides. A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In some embodiments, it is contemplated that the specific interleukin-15 (IL-15) antagonist polypeptide of the present invention is modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain. For example, Pegylation is a well established and validated approach for the modification of a range of polypeptides. The benefits include among others: (a) markedly improved circulating half-lives in vivo due to either evasion of renal clearance as a result of the polymer increasing the apparent size of the molecule to above the glomerular filtration limit, and/or through evasion of cellular clearance mechanisms; (b) reduced antigenicity and immunogenicity of the molecule to which PEG is attached; (c) improved pharmacokinetics; (d) enhanced proteolytic resistance of the conjugated protein; and (e) improved thermal and mechanical stability of the PEGylated polypeptide.

Another object of the invention relates to an isolated, synthetic or recombinant nucleic acid encoding for a specific interleukin-15 (IL-15) antagonist polypeptide of the present invention.

As used herein, the term "nucleic acid" has its general meaning in the art and refers to a DNA or RNA molecule. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fiuorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

In some embodiments, the nucleic acid of the present invention is a DNA or RNA molecule, which may be included in any suitable vector, such as a plasmid, cosmid, episome, artificial chromosome, phage or a viral vector. The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, another object of the invention relates to a vector comprising a nucleic acid of the invention.

Such vectors may comprise regulatory elements, such as a promoter, enhancer, terminator and the like, to cause or direct expression of said polypeptide upon administration to a subject. The vectors may further comprise one or several origins of replication and/or selectable markers. The promoter region may be homologous or heterologous with respect to the coding sequence, and provide for ubiquitous, constitutive, regulated and/or tissue specific expression, in any appropriate host cell, including for in vivo use. Examples of promoters include bacterial promoters (T7, pTAC, Trp promoter, etc.), viral promoters (LTR, TK, CMV-IE, etc.), mammalian gene promoters (albumin, PGK, etc), and the like. Examples of plasmids include replicating plasmids comprising an origin of replication, or integrative plasmids, such as for instance pUC, pcDNA, pBR, and the like. Examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

Another object of the present invention relates to a host cell which has been transfected, infected or transformed by a nucleic acid molecule and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acid molecule of the invention may be used to produce a specific interleukin-15 (IL-15) antagonist polypeptide of the present invention in a suitable expression system. The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). The construction of expression vectors in accordance with the invention, and the transformation of the host cells can be carried out using conventional molecular biology techniques. The specific interleukin-15 (IL-15) antagonist polypeptide of the present invention, can, for example, be obtained by culturing genetically transformed cells in accordance with the invention and recovering the polypeptide expressed by said cell, from the culture. They may then, if necessary, be purified by conventional procedures, known in themselves to those skilled in the art, for example by fractional precipitation, in particular ammonium sulfate precipitation, electrophoresis, gel filtration, affinity chromatography, etc. In particular, conventional methods for preparing and purifying recombinant proteins may be used for producing the polypeptides in accordance with the invention. Thus the present invention also relates to a method for producing a recombinant host cell expressing a specific interleukin-15 (IL-15) antagonist polypeptide of the present invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete the polypeptide of the invention. Such recombinant host cells can be used for the production of polypeptides and fusions proteins of the present invention. The invention further relates to a method of producing a specific interleukin-15 (IL-15) antagonist polypeptide of the present invention, which method comprises the steps consisting of: (i) culturing a transformed host cell according to the invention under conditions suitable to allow expression of said polypeptide or fusion protein; and (ii) recovering the expressed polypeptide or fusion protein.

The specific interleukin-15 (IL-15) antagonist polypeptide of the present invention is particularly suitable for therapeutic purposes including the treatment of autoimmune diseases and inflammatory diseases.

Accordingly a further object of the present invention relates to the specific interleukin-15 (IL-15) antagonist polypeptide of the present invention for use as a drug.

A further object of the present invention relates to a method of suppressing the immune response in a patient by administering a dose of a specific interleukin-15 (IL-15) antagonist polypeptide of the present invention, and thereby modulates IL-15 dependent immune responses.

In particular, the method of the present invention is suitable to treat a patient suffering from an autoimmune disease. Examples of autoimmune disease include, without limitation, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/Anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, autoimmune urticaria, axonal and neuronal neuropathies, Behcet's disease, bullous pemphigoid, autoimmune cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic fasciitis, erythema nodosum, experimental allergic encephalomyelitis, Evans syndrome, fibromyalgia, fibrosing alveolitis, giant cell arteritis (temporal arteritis), glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, hypergammaglobulinemia, idiopathic thrombocytopenic purpura (ITP), IgA nephropathy, IgG4-related sclerosing disease, immunoregulatory lipoproteins, inclusion body myositis, inflammatory bowel disease, insulin-dependent diabetes (type 1), interstitial cystitis, juvenile arthritis, Kawasaki syndrome, Lambert-Eaton syndrome, leukocytoclastic vasculitis, lichen planus, lichen sclerosus, ligneous conjunctivitis, linear IgA disease (LAD), lupus (SLE), Lyme disease, Meniere's disease, microscopic polyangiitis, mixed connective tissue disease (MCTD), monoclonal gammopathy of undetermined significance (MGUS), Mooren's ulcer, Mucha-Habermann disease, multiple sclerosis, myasthenia gravis, myositis, narcolepsy, neuromyelitis optica (Devic's), autoimmune neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis *nodosa*, type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/Giant cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, Waldenstrom's macroglobulinemia (WM), and Wegener's granulomatosis [Granulomatosis with Polyangiitis (GPA)].

More particularly, the method of the present invention is particularly suitable to treat a patient who is suffering from an autoimmune disease, including but not limited to the following: (1) a rheumatic disease such as rheumatoid arthritis, systemic lupus erythematosus, Sjogren's syndrome, scleroderma, mixed connective tissue disease, dermatomyositis, polymyositis, Reiter's syndrome or Behcet's disease (2) type II diabetes (3) an autoimmune disease of the thyroid, such as Hashimoto's thyroiditis or Graves' Disease (4) an autoimmune disease of the central nervous system, such as multiple sclerosis, myasthenia gravis, or encephalomyelitis (5) a variety of phemphigus, such as phemphigus vulgaris, phemphigus vegetans, phemphigus *foliaceus*, Senear-Usher syndrome, or Brazilian phemphigus, (6) psoriasis, and (7) inflammatory bowel disease (e.g., ulcerative colitis or Crohn's Disease).

The administration of the specific interleukin-15 (IL-15) antagonist polypeptide of the present invention may also be useful in the treatment of acquired immune deficiency syndrome (AIDS).

Another use for the specific interleukin-15 (IL-15) antagonist polypeptide of the present invention includes the treatment of late phase HTLV (human T-cell lymphotrophic virus) I-induced adult T-cell leukemia-lymphoma, See Burton et al., Proc. Natl. Acad. Sci., 91:4935 (1994).

In some embodiments, the method of the present invention is used to treat a patient who has received a transplant of biological materials, such as an organ, tissue, or cell transplant. For example, the specific interleukin-15 (IL-15) antagonist polypeptide of the present invention may be particularly suitable, in promoting graft survival (allograft or xenograft). Typically the subject may have been transplanted with a graft selected from the group consisting of heart, kidney, lung, liver, pancreas, pancreatic islets, brain tissue, stomach, large intestine, small intestine, cornea, skin, trachea, bone, bone marrow, muscle, or bladder. The method of the present invention is also particularly suitable for preventing or suppressing an immune response associated with rejection of a donor tissue, cell, graft, or organ transplant by a recipient subject. Graft-related diseases or disorders include graft versus host disease (GVHD), such as associated with bone marrow transplantation, and immune disorders resulting from or associated with rejection of organ, tissue, or cell graft transplantation (e.g., tissue or cell allografts or xenografts), including e.g., grafts of skin, muscle, neurons, islets, organs, parenchymal cells of the liver, etc. Thus the method of the invention is useful for preventing Host-Versus-Graft-Disease (HVGD) and Graft-Versus-Host-Disease (GVHD). The specific interleukin-15 (IL-15) antagonist polypeptide of the present invention may be administered to the subject before, during and/or after transplantation (e.g., at least one day before transplantation, at least one day after transplantation, and/or during the transplantation procedure itself). In some embodiments, the specific interleukin-15 (IL-15) antagonist polypeptide of the present invention may be administered to the subject on a periodic basis before and/or after transplantation.

Typically, the specific interleukin-15 (IL-15) antagonist polypeptide of the present invention is typically administered in a therapeutically effective amount. By a "therapeutically effective amount" is meant a sufficient amount of the fusion protein or the antagonist of the invention to treat and/or to prevent the disease at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the disease being treated and the severity of the disease; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

A further object of the invention relates to pharmaceutical compositions comprising a specific interleukin-15 (IL-15) antagonist polypeptide of the present invention optionally with a pharmaceutically acceptable carrier or excipient. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The specific interleukin-15 (IL-15) antagonist polypeptide of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. The specific interleukin-15 (IL-15) antagonist polypeptide of the present invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

Figure 1:
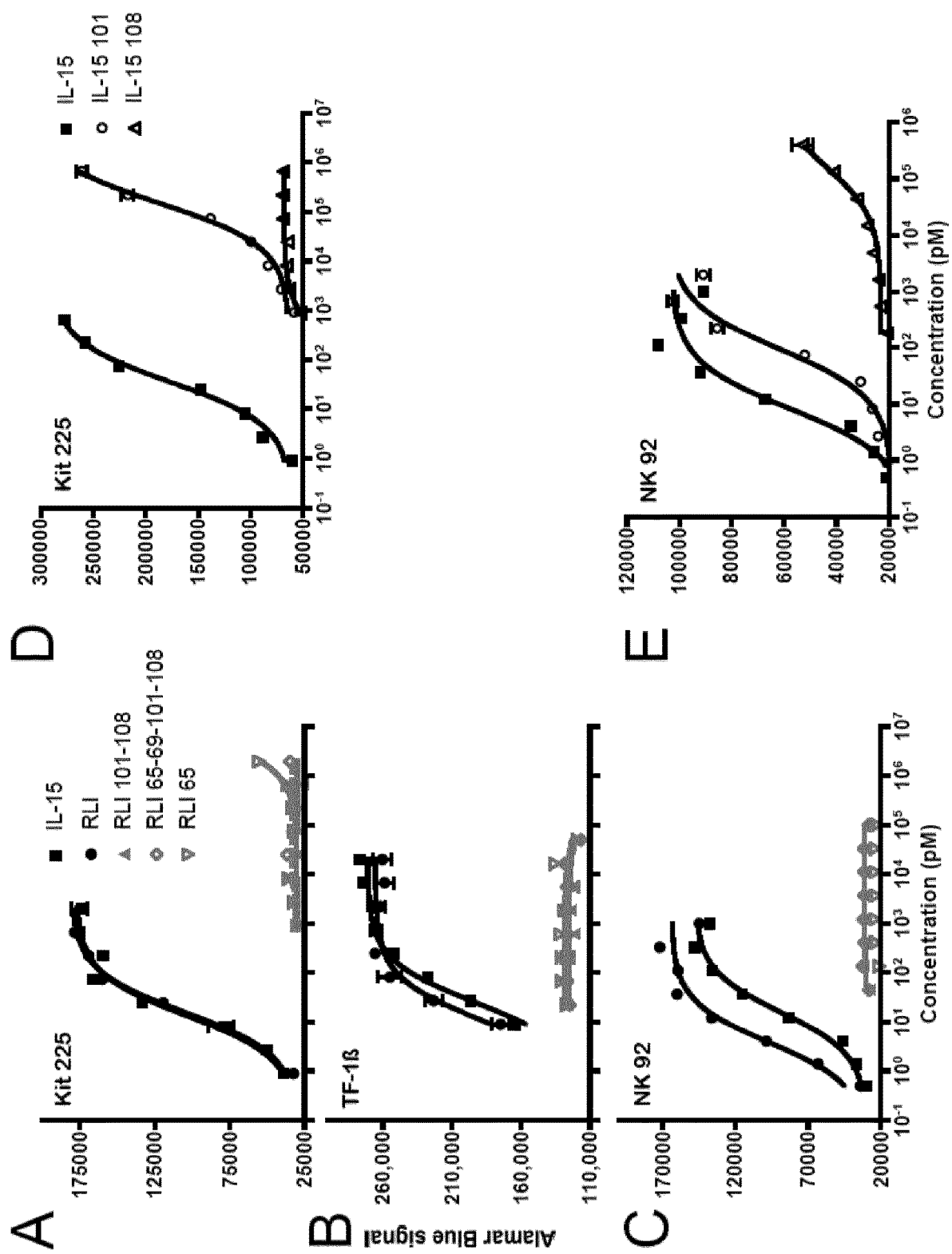

FIG. 1. Effect of mutated RLI or mutated IL-15 on cell proliferation. Kit-225 (A), TF-1β (B) and NK-92 (C) cells were cultured for 72 h with increasing concentrations of IL-15 (.box-solid.), RLI (.circle-solid.), RLI 101-108 (.tangle-solidup.), RLI 65-69-101-108 (.diamond.), RLI 65 (.gradient.). Kit-225 (D) and NK-92 (E) cells were cultured for 72 h with increasing concentrations of IL-15 (.box-solid.), IL-15 101 (.largecircle.) or IL-15 108 (.DELTA.). Cell proliferation was quantified by ALAMARBLUE® assay, a fluorometric/colorimetric growth assay.

Figure 2:
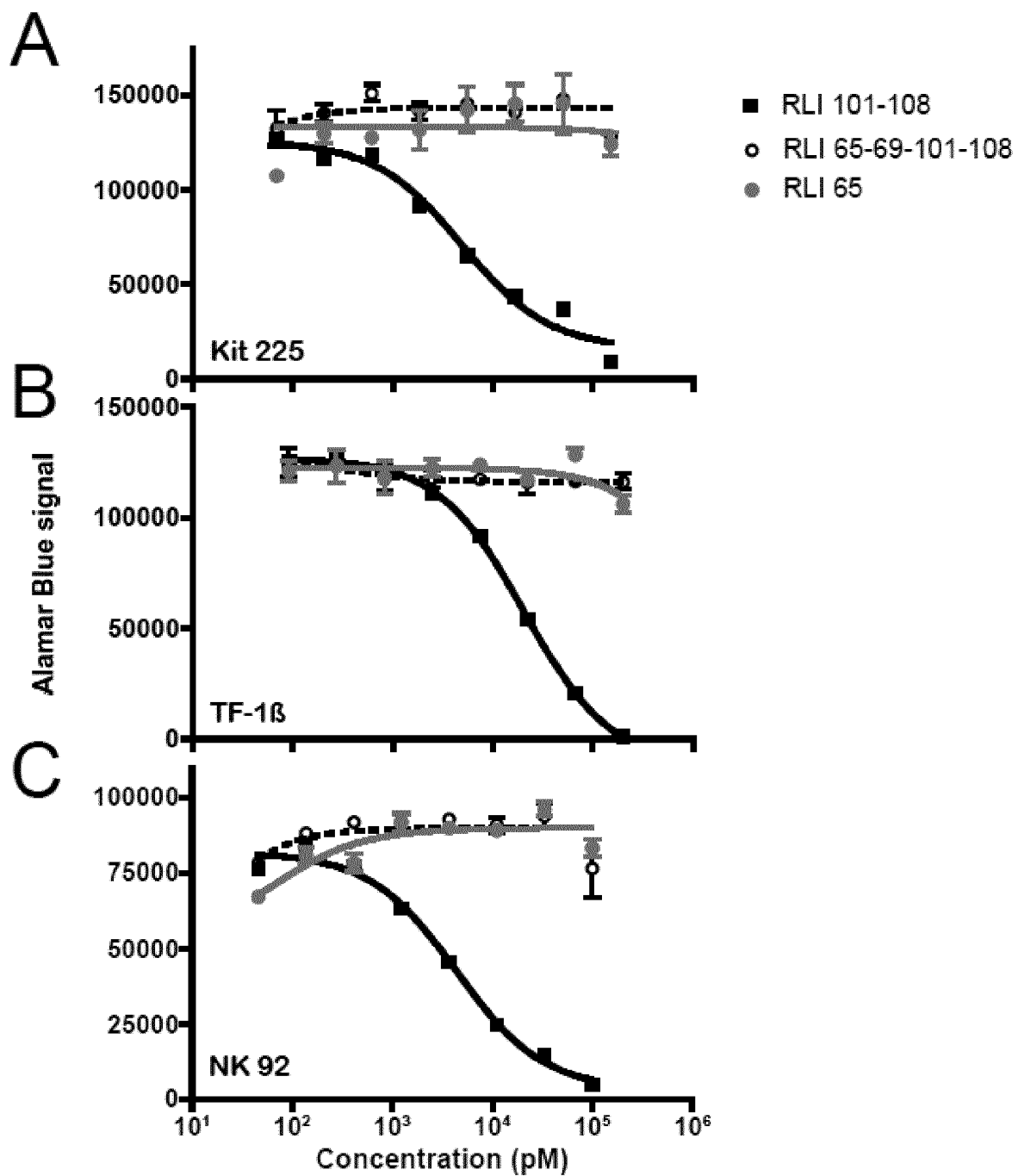

FIG. 2. Effect of mutated RLI on RLI induced cell proliferation. Kit-225 (A), (A), TF-1.beta. (B) and NK-92 (C) cells were cultured for 72 h with a fixed concentration of RLI (40 pM for Kit-225 and TF-1B; 10 pM for NK-92) and increasing concentrations of RLI 101-108 (.box-solid.), RLI 65-69-101-108 (0) or RLI 65 (.circle-solid.). Cell proliferation was quantified by ALAMARBLUE® assay fluorometric/colorimetric growth assay.

Figure 3:
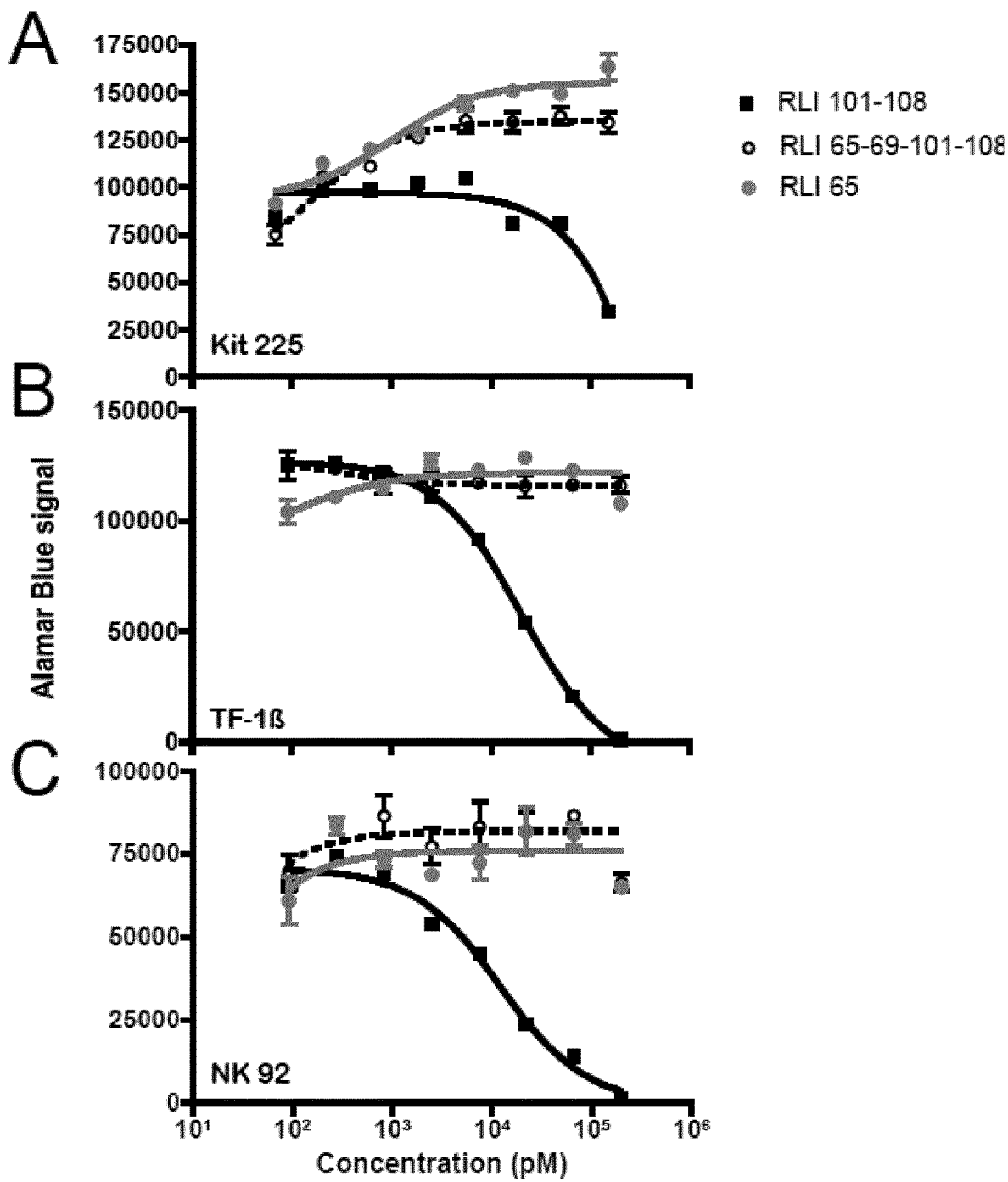

FIG. 3. Effect of mutated RLI on IL-15 induced cell proliferation. Kit-225 (A), (A), TF-1.beta. (B) and NK-92 (C) cells were cultured for 72 h with a fixed concentration of IL-15 (80 pM for Kit-225, 40 pM for TF-1B and NK-92) and increasing concentrations of RLI 101-108 (.box-solid.), RLI 65-69-101-108 (.largecircle.) or RLI 65 (.circle-solid.). Cell proliferation was quantified by ALAMARBLUE® assay, a fluorometric/colorimetric growth assay.

Figure 4:
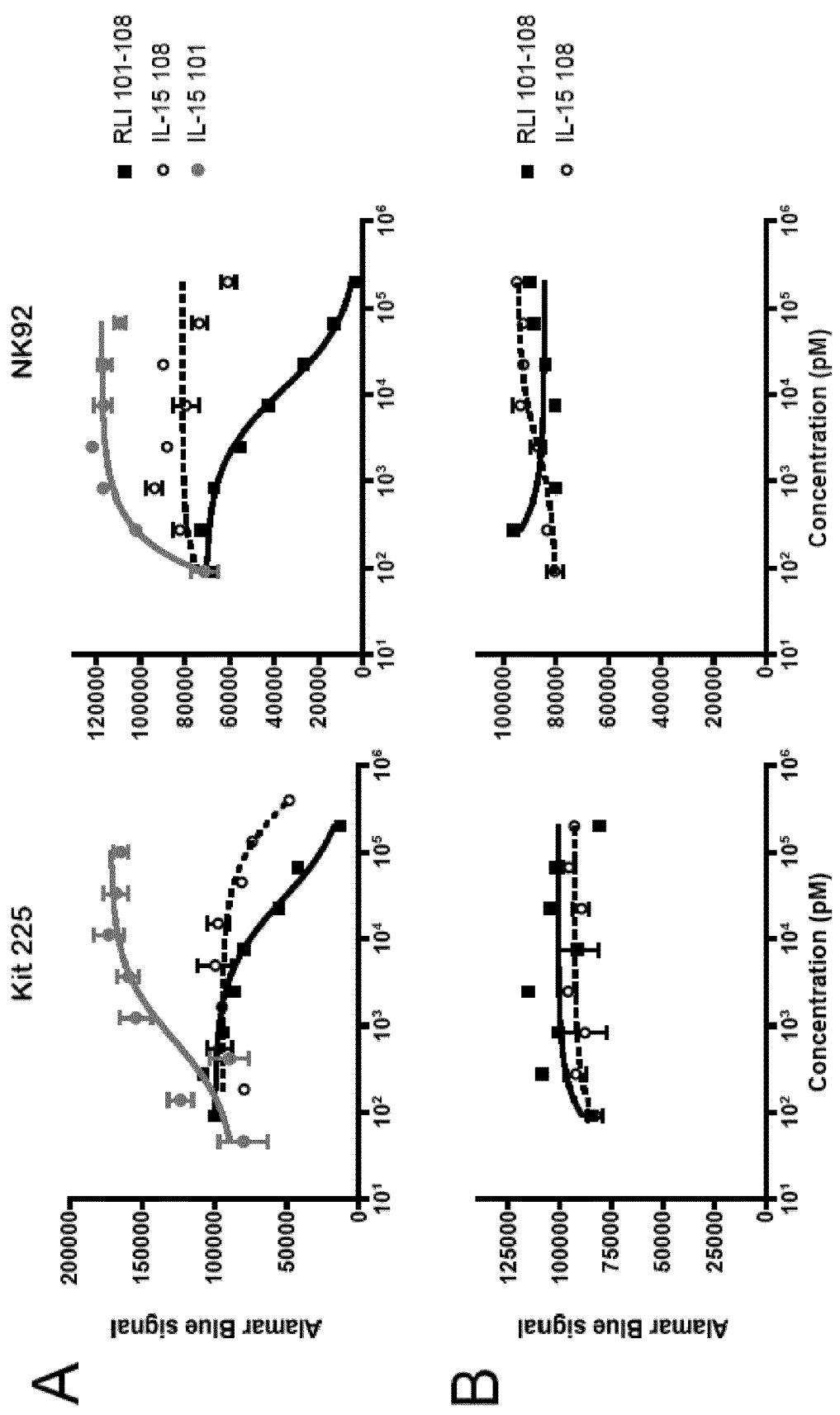

FIG. 4. Effect of mutated IL-15 on IL-15 or IL-2 induced cell proliferation. Kit-225 (left panels) and NK-92 (right panels) cells were cultured for 72 h with a fixed concentration of IL-15 (A) or IL-2 (B) (80 pM for Kit-225 and 40 pM for NK-92) and increasing concentrations of RLI 101-108 (.box-solid.), IL-15 101 (.circle-solid.) or IL-15 108 (.largecircle.). Cell proliferation was quantified by ALAMARBLUE® assay, a fluorometric/colorimetric growth assay.

Figure 5:
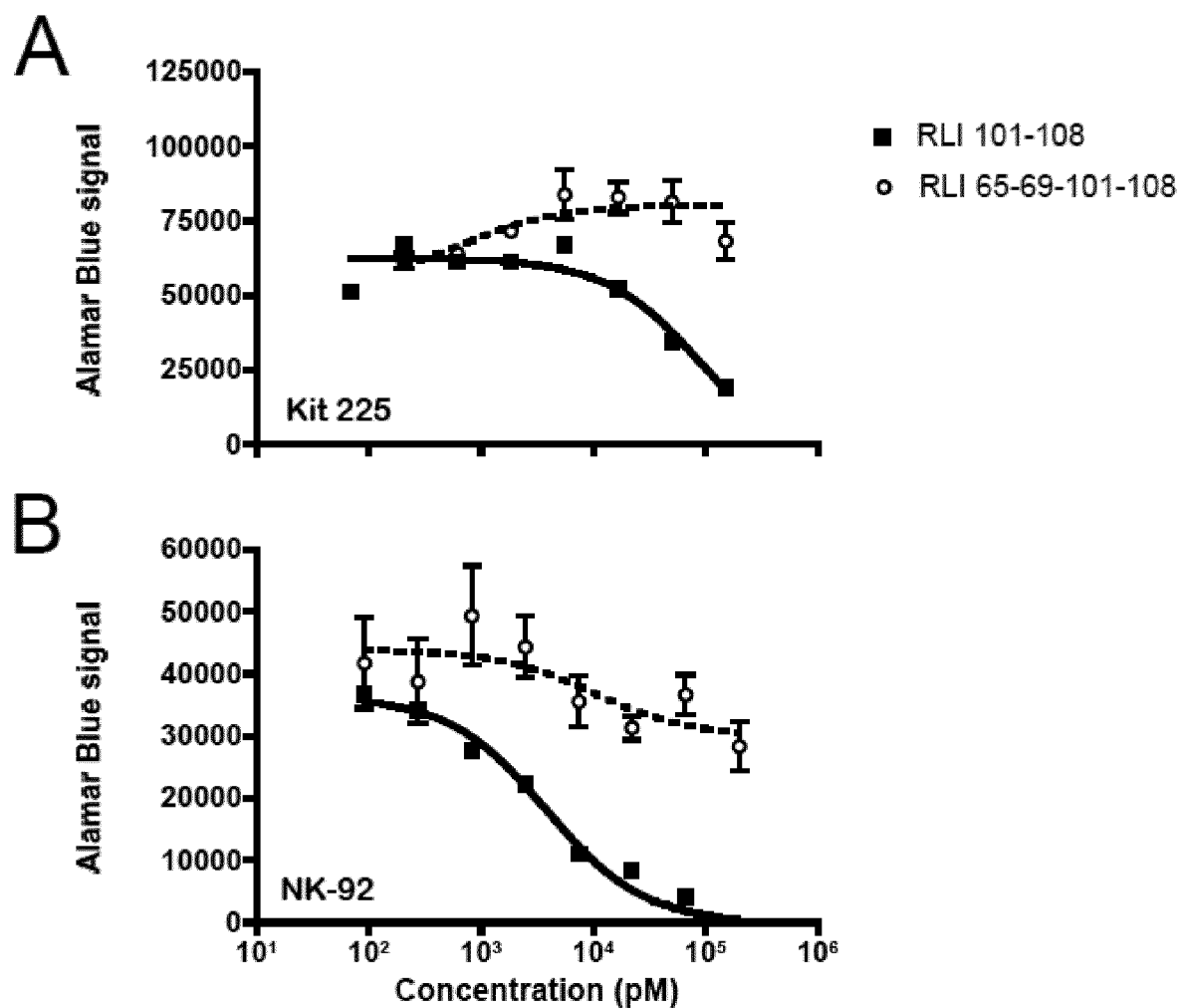

FIG. 5. Effect of mutated RLI on IL-2 induced cell proliferation in the presence of IL-2Ralpha blocking antibody. Kit-225 (A) or NK-92 (B) cells were cultured for 72 hr with a fixed concentration of IL-2 (500 or 80 pM respectively), 33B3.1 blocking antibody (5 nM) and increasing concentrations of RLI 101-108 (.box-solid.) or RLI 65-69-101-108 (largecircle.). Cell proliferation was quantified by ALAMARBLUE® assay, a fluorometric/colorimetric growth assay.

Figure 6:
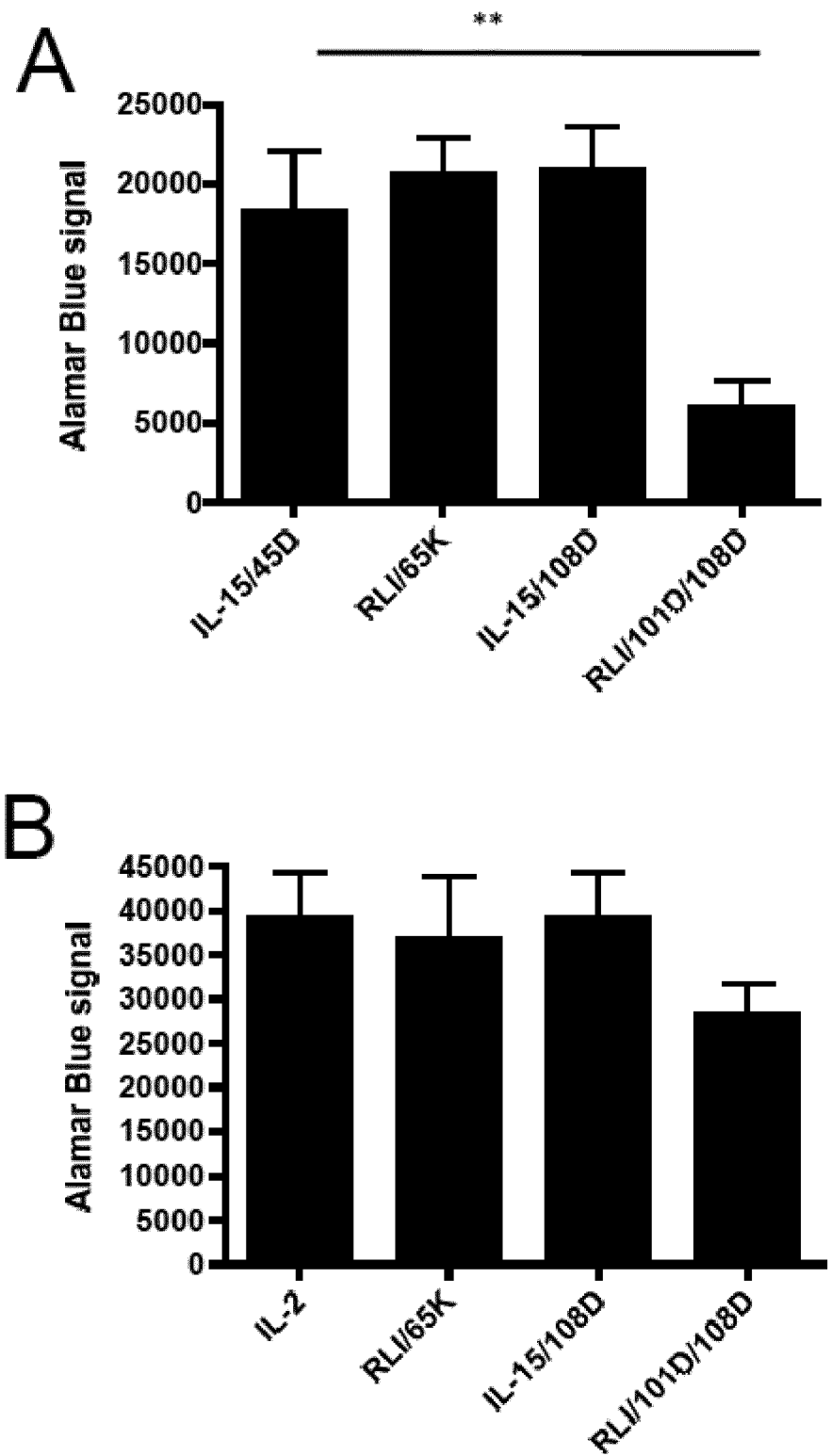

FIG. 6. Effect of mutated RLI before a brief stimulation of NK-92 cells by IL-15 or IL-2. NK-92 cells were incubated with 200 nM of mutated RLI for 30 min before a 30 min stimulation with IL-15 (A) or IL-2 (B) (40 pM). Cells were then cultivated for 24 h and cell proliferation was quantified by ALAMARBLUE® assay, a fluorometric/colorimetric growth assay.

Figure 7:
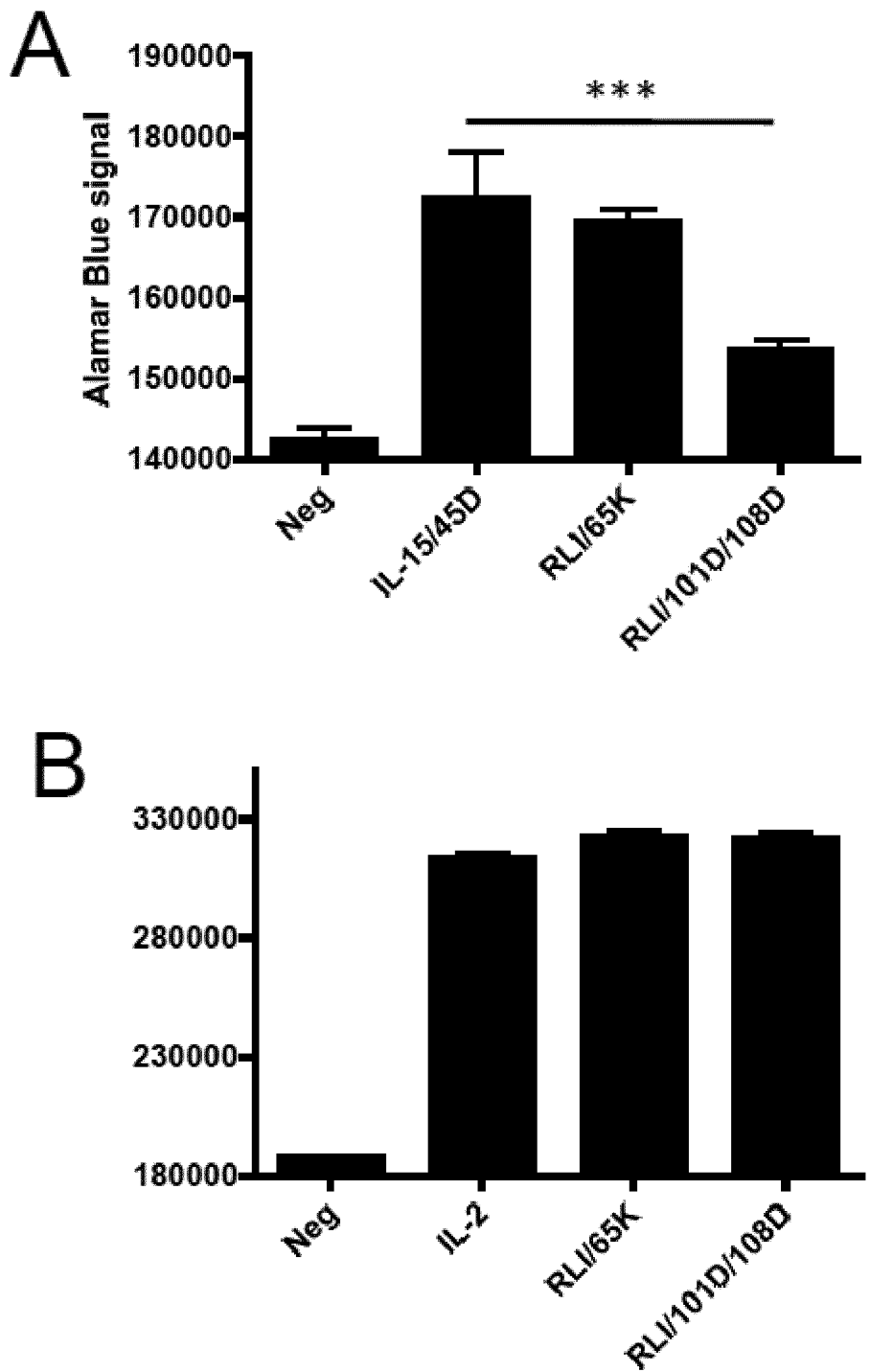

FIG. 7. Effect of mutated RLI after a brief stimulation of NK-92 cells by IL-15 or IL-2. NK-92 cells were incubated with 1 nM of IL-15 (A) or IL-2 (B) for 30 min. After 2 washes, cells were cultivated for 24 h with fixed concentration of mutated RLI (200 nM). Cell proliferation was quantified by ALAMARBLUE® assay, a fluorometric/colorimetric growth assay.

Figure 8:
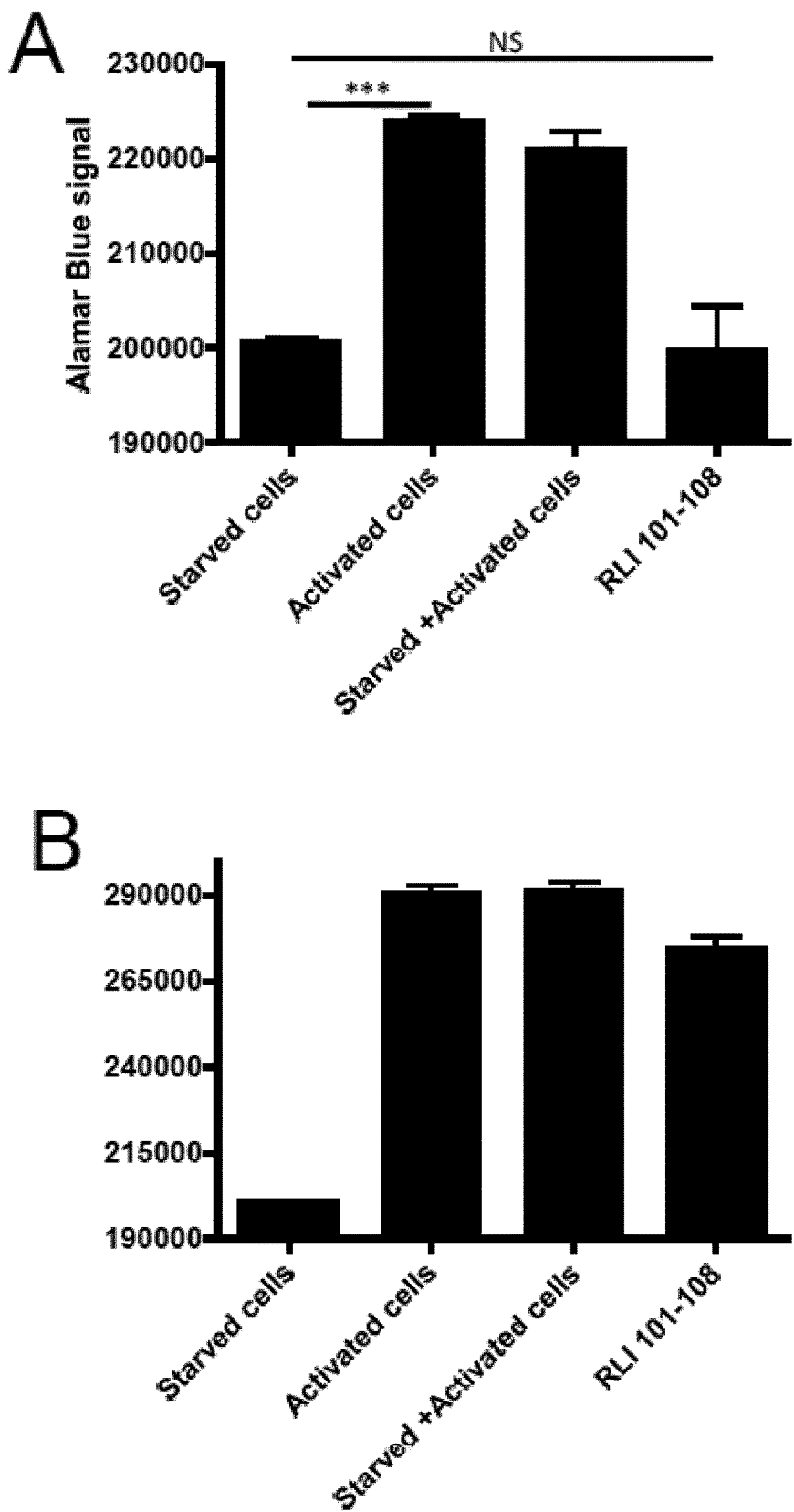

FIG. 8. Effect of mutated RLI on the propagation of metabolic activity of NK-92 cells. NK-92 cells were stimulated for 30 min with IL-15 (A) or IL-2 (B) (1 nM). After 2 washes, stimulated cells were cultivated with cytokine starved NK-92 cells in the presence of mutated RLI (50 nM) for 24 h. Cell proliferation was quantified by ALAMARBLUE® assay, a fluorometric/colorimetric growth assay.

Figure 9:
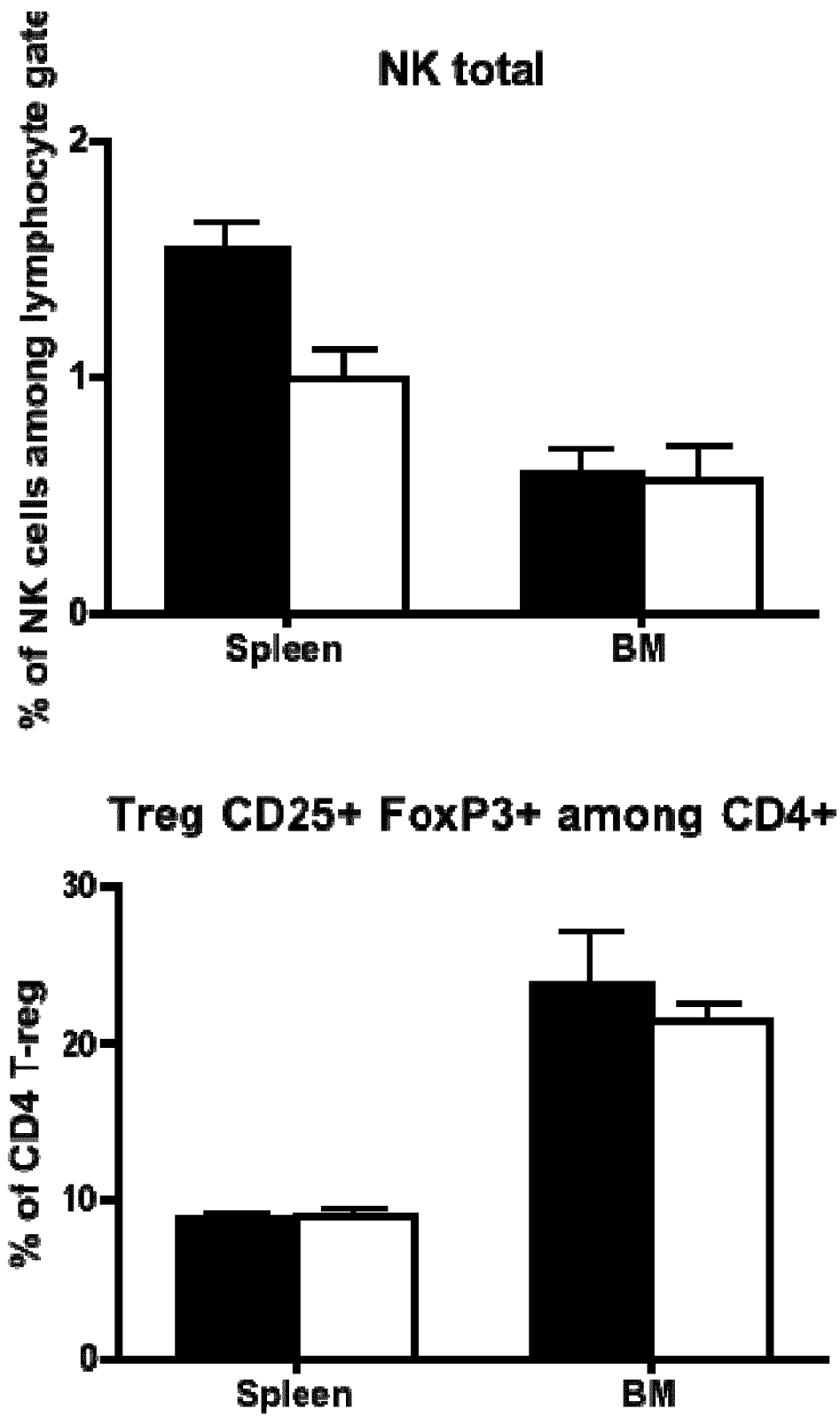

FIG. 9. In vivo effect of mutated RLI on NK and CD4 T-reg homeostasis. PBS or mutated RLI were injected every day for 3 days (2 ug per injection). Mice were sacrificed one day later. Spleen and bone marrow were collected, and cells were isolated. NK cells were identified as NK1.1+ CD3− and T-reg cells were CD3+ CD4+ CD25+ FoxP3+.

FIG. 10. Molecular modelling based predicted effects of different mutations at position Q101 or Q108 on the antagonistic properties of IL-15.

FIG. 11. SPR sensorgrams of the binding (association and dissociation phases) of increasing concentrations of indicated molecules (3.1, 6.2, 12.5, 25, 50 and 100 nM) to immobilized CD122 (A and C) or Fc-IL-15Rα (B and D) chains. (E) SPR sensorgrams of sequential binding of increasing concentrations of wt.RLI or $RLI_{Q108D}$ to immobilized CD122 chain, followed by the binding of CD132 chain.

Figure 12A:
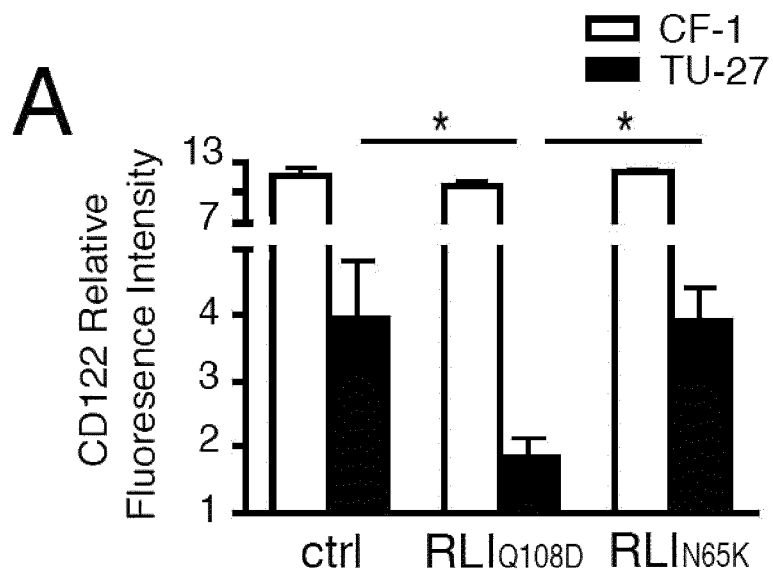
Figure 12B:
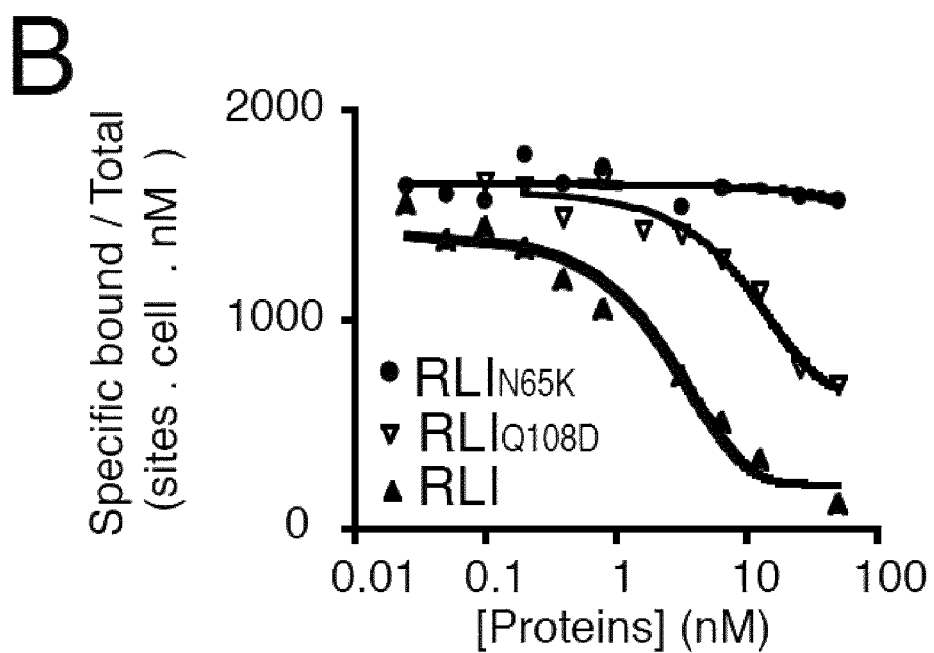

FIG. 12 (A) Flow cytometric analysis of CD122 expression on the surface of $RLI_{Q108D}$ or $RLI_{N65K}$ pre-treated NK-92 cells revealed by blocking TU-27 or non-blocking CF-1 anti-CD122 mAbs. (B) Competition studies of indicated molecules with radioiodinated wt.RLI (1 nM) binding to NK-92 cells.

FIG. 13. (A) Proliferation assay of Kit225 or (B) NK-92 cells cultured with increasing concentrations of indicated molecules.

Figure 14A:
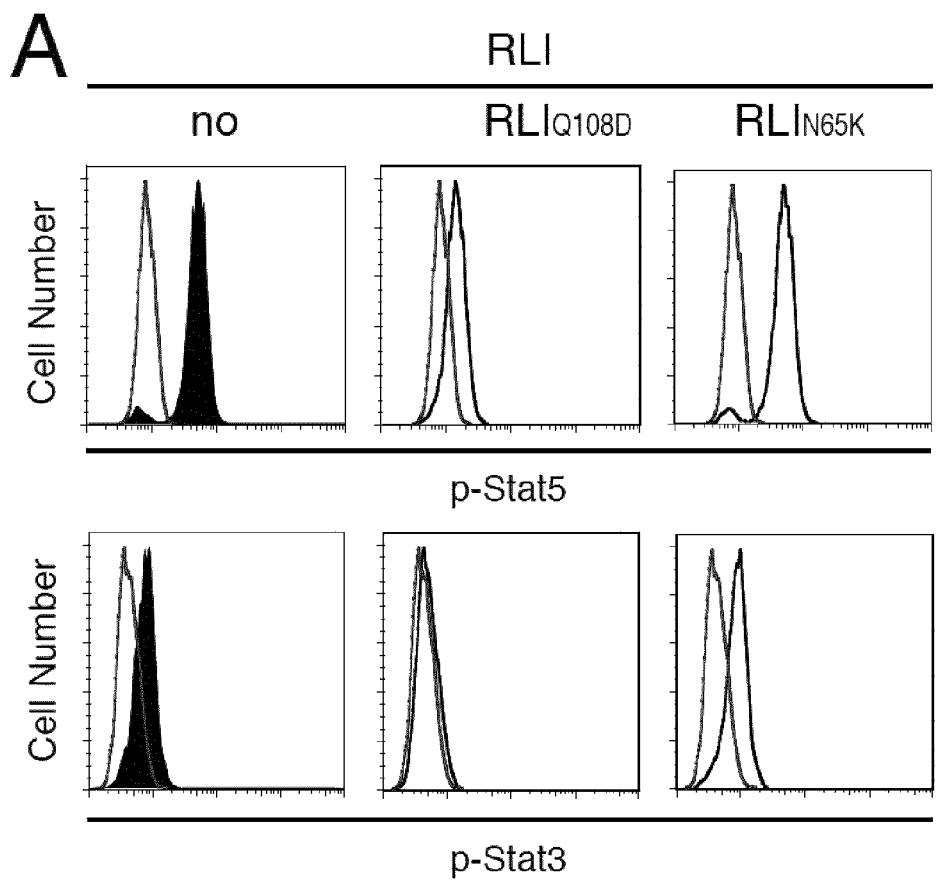
Figure 14B:
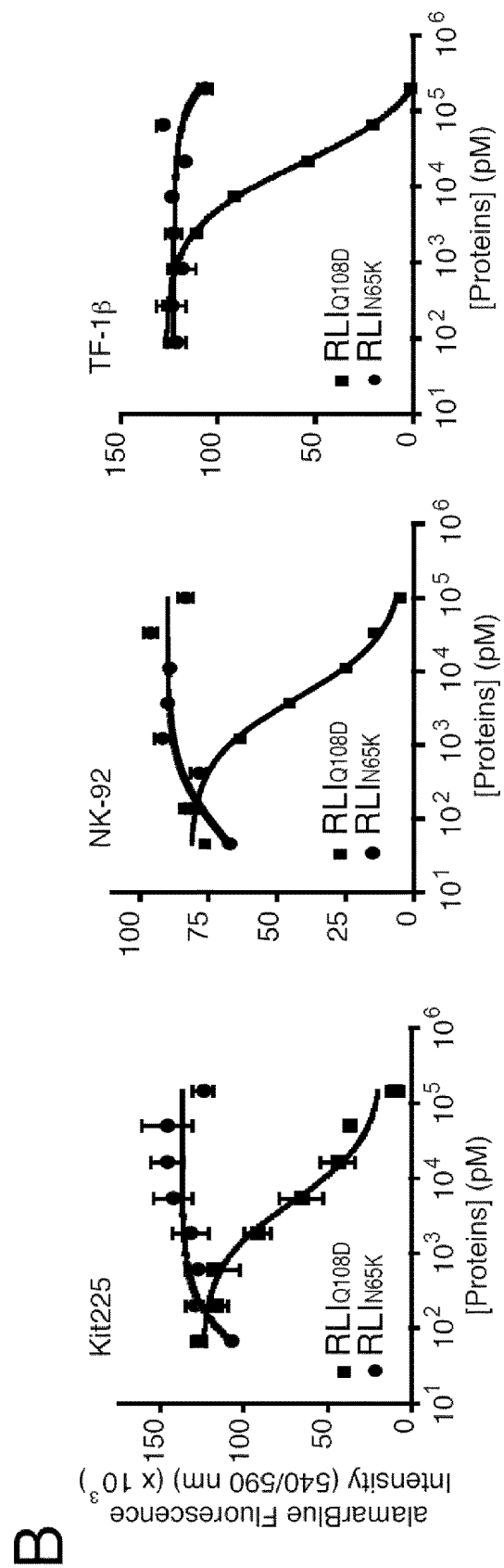

FIG. 14. (A) Flow cytometric analyses of wt.RLI-induced Stat5 and Stat3 phosphorylations in the absence or in the presence of $RLI_{Q108D}$ or $RLI_{N65K}$. Isotype control is shown. (B) Proliferation assay of Kit225, NK-92 and TF-1β cells cultured with a fixed concentration of wt.RLI (40 pM) and increasing concentrations of $RLI_{Q108D}$ or $RLI_{N65K}$.

Figure 15A:
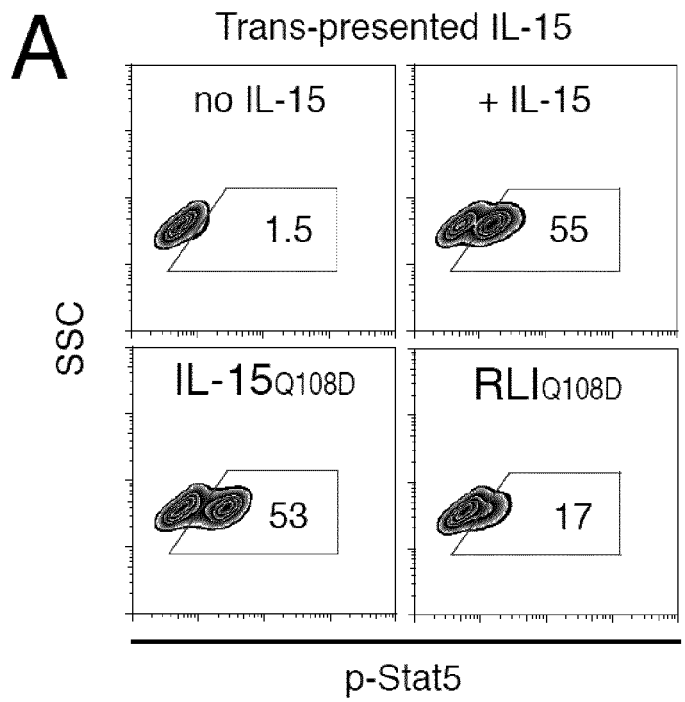
Figure 15B:
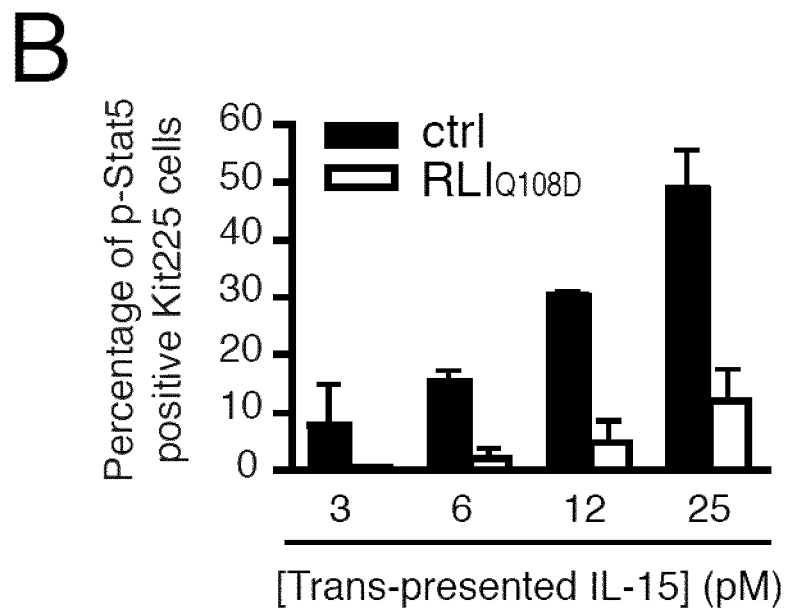

FIG. 15. (A) Analysis of p-Stat5 expression within Kit225 responding cells following 1 h co-culture with IL-15 (25 pM) loaded or un-loaded stably transfected IL-15R⟨ HeLa presenting cells in the presence or in the absence of 50 nM of $RLI_{Q108D}$ or $IL-15_{Q108D}$. Numbers indicate the percentage of cells in the indicated gate. (B) Percentage of p-Stat5 positive Kit225 responding cells in response to increasing concentrations of IL-15 loaded on IL-15R⟨ HeLa presenting cells in the presence of $RLI_{Q108D}$ (100 nM).

Figure 16:
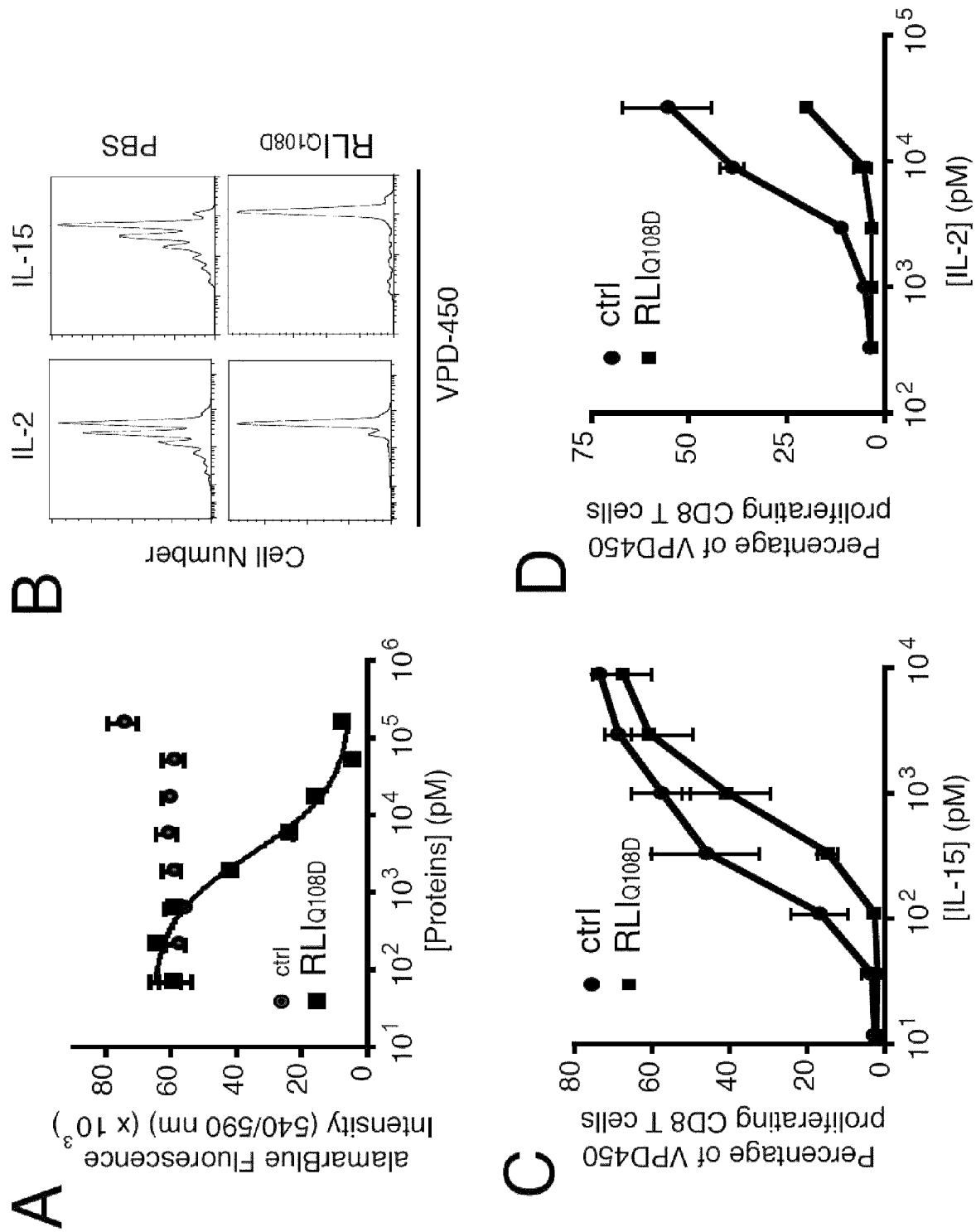

FIG. 16. (A) Proliferation assay of TF-1β cells cultured with a fixed concentration of IL-2 (1 nM) and increasing concentrations of $RLI_{Q108D}$. (B) CD8 T cells were stimulated with 5 nM of indicated cytokines in the presence or in the absence of $RLI_{Q108D}$ (50 nM). (C) The proliferation of human PBMCs was evaluated by flow cytometry. Isolated PBMCs were labeled by VPD-450 and cultured with increasing concentrations of IL-15 or (D) IL-2 in the presence or in the absence of 100 nM of $RLI_{Q108D}$. CD8 T cells were identified as CD3+ CD8+ cells.

Figure 17:
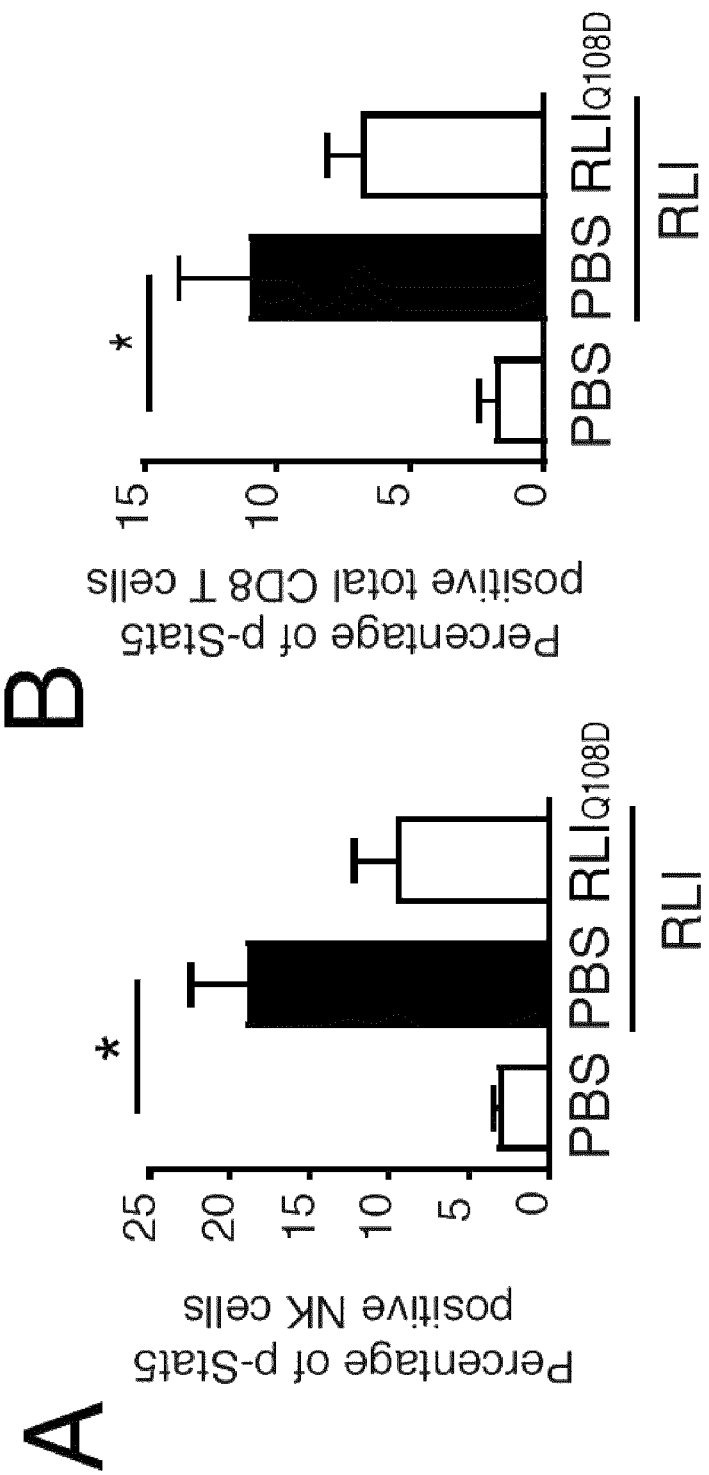

FIG. 17. (A) Analysis of p-Stat5 within splenic NKp46+ CD3− NK and (B) CD8 T cells from mice treated as indicated. (n=5 per conditions).

FIG. 18. IL-2Rα impairs $RLI_{Q108D}$ inhibition of IL-2 signaling. (A) Inhibition assay of IL-15- and IL-2-induced Stat5 phosphorylation within Kit225 cells treated with $RLI_{Q108D}$ (white bars) for 1 h or not (black bars), revealed by alpha screen technology. (B) Proliferation assay of Kit225 cells cultured with a fixed concentration of IL-2 (80 pM) and increasing concentrations of $RLI_{Q108D}$ or $RLI_{N65K}$. (C) Proliferation assay of Kit225 cells cultured with a fixed concentration of IL-2 (80 pM) and 33B3.1 anti-CD25 mAb (66 nM) and increasing concentrations of $RLI_{Q108D}$ or $RLI_{N65K}$. (D) Proliferation assay of Kit225 cells cultured with a fixed concentration of IL-15 (40 pM) and increasing concentrations of $RLI_{Q108D}$ and/or $IL-15_{Q108D}$. (E) The proliferation of NK cells from human PBMCs was evaluated by flow cytometry. Isolated VPD-450-labeled PBMCs were cultured with a fixed concentration of IL-15 or (F) IL-2 in the presence or in the absence of 33B3.1 anti-CD25 mAb and increasing concentrations of $RLI_{Q108D}$. NK cells were identified as CD3− NKp46+ cells. (G) IL-2-induced proliferation of CD4 T cells was evaluated by VPD-450 dilution over CD25 expression in the presence or in the absence of $RLI_{Q108D}$. (H) IL-2-induced proliferation of CD25− or (I) CD25+CD4+ CD3+ T cells was evaluated by VPD-450 dilution over CD25 expression in the presence or in the absence of 100 nM of $RLI_{Q108D}$.

Figure 19:
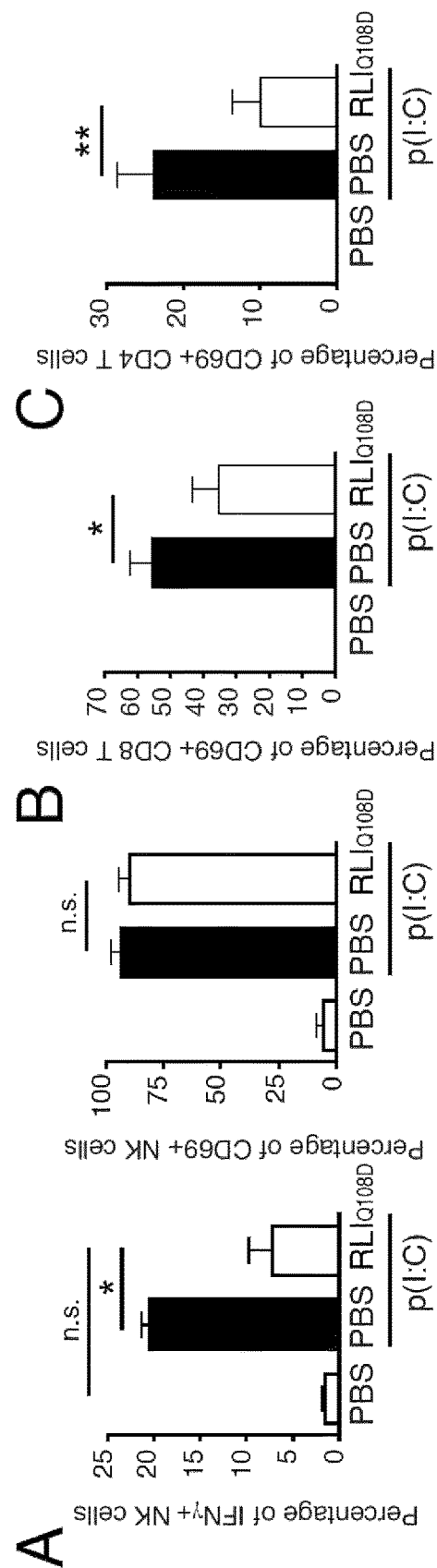

FIG. 19. (A) Mice were treated or not with $RLI_{Q108D}$ prior from administrating poly(I:C). NK cells in the blood from mice were analyzed for IFNγ and CD69 expression by flow cytometry. (B) Analysis of CD69 expression on CD8 and (C) CD4 T cells in the blood from mice treated as indicated.

FIG. 20. (A) Percentage of FoxP3+ CD25+ CD4 T cells among total CD4 T cells from human PBMCs was analyzed by flow cytometry. (B) Ratio of proliferative CD4 regulatory T-cells over CD8 T cells among human PBMCs stimulated with indicated concentrations of IL-2 in the presence or in the absence of $RLI_{Q108D}$. (C) Splenic CD44+ CD8+ T cells or (D) CD3-NKp46+ NK cells from mice treated as indicated were analyzed by flow cytometry. (E) Numbers of splenic NK cells at the indicated stages of maturation from mice treated as indicated. (F) Splenic FoxP3+ CD25+ CD4 T cells were analyzed by flow cytometry and (G) graph showing the ratio of CD4 regulatory T-cells over NK cells among lymphoid gate.

Figure 21:
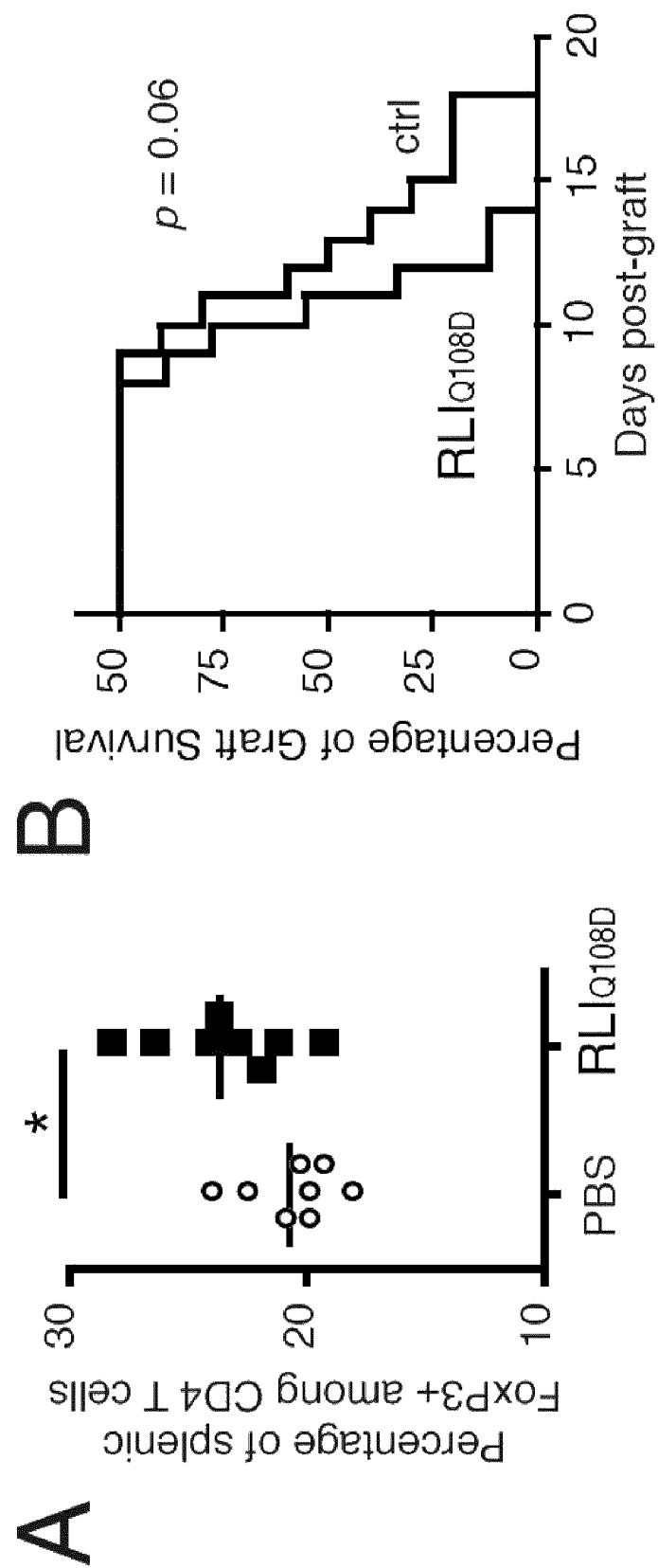

FIG. 21. (A) Twenty weeks old mice were treated with $RLI_{Q108D}$ and splenic FoxP3+CD25+ CD4 T cells were analyzed. (B) Skin from Balb/c mice was grafted to DBA/2 recipient mice. Mice (n=10, per conditions) were treated daily with 10 μg of $RLI_{Q108D}$ and graft survival was monitored.

EXAMPLE 1

Material & Methods

Cell Culture

The non adherent Kit-225 human T lymphoma cell line, obtained from Dr. D. Cantrell (University of Dundee, Scotland, U.K.), was cultured in RPMI-1640 medium (Gibco-Invitrogen) containing 6% heat-inactivated fetal calf serum, 2 mM glutamine, and 5 ng/mL human rIL-2. The nonadherent TF-113 human erythroleukemia cell line, kindly provided by Dr. B. Azzarone (Institut Gustave-Roussy, Villejuif, France) was culture in RPMI 1640 medium containing 10% heat inactivated fetal calf serum, 2 mM glutamine, 1 ng/mL GM-CSF ans 250 μg/mL geneticin. The NK-92 cell line, kindly provided by Henri Vié (Inserm U892, Nantes, France), was cultured in RPMI-1640 medium (Gibco-Invitrogen) containing 10% heat-inactivated human serum, 2 mM glutamine, and 5 ng/mL human rIL-2.

Proliferation Assays

The proliferative responses of Kit-225, TF-113 and NK-92 cells to cytokine was quantified by ALAMARBLUE® assay, a fluorometric/colorimetric growth assay (AbD serotec, Kidlington, UK). Briefly, cells were starved in the culture medium without cytokine during 24 hrs for Kit-225 or 5 hrs for TF-113 and NK-92. Cells were plated at $110.sup.4$ cells in $100.mu.l$ and cultured for 48 h in medium supplemented with increasing concentrations of tested protein, or in medium supplemented with a fixed concentration of human rIL-15, human rIL-2 or RLI and increasing concentrations of tested antagonist. Cells were pulsed for 6 h with $10.mu.L$ per well of ALAMARBLUE®, a fluorometric/colorimetric indicator. Cell proliferation was assessed by measuring fluorescence at 550/590 nm using Enspire plate reader (Perkin elmer, Hopkinton Mass., USA).

Short Cytokine Stimuli

The proliferative responses of Kit-225, TF-1.beta. and NK-92 cells to a short cytokine stimulus was quantified by ALAMARBLUE® assay, a fluorometric/colorimetric growth assay. Briefly, cells were starved in the culture medium without cytokine during 24 h. They were incubated at $210.sup.5$ cells per mL with 40 pM or 1 nM of human rIL-15 or rIL-2 for 30 min, washed twice and cultured for 24 h in medium supplemented with fixed concentrations of tested protein. Cell metabolic activity was assayed by ALAMARBLUE®, a fluorometric/colorimetric indicator, as described previously. In a second set of experiments, the 30 min cytokine stimuli were realized on cells in contact with tested protein since 30 min.

Propagation of Viability Signal

The propagation of cell metabolic activity was detected by ALAMARBLUE® assay, a fluorometric/colorimetric growth assay. Briefly, cells were starved in the culture medium without cytokine during 24 hrs. Cells were incubated $210.sup.5$ cells per mL with 1 nM of human rIL-15 or rIL-2 for 30 minutes, washes twice and $210.sup.4$ of these activated cells were cultured 24 hrs with $210.sup.4$ of starved in the presence of antagonist. Cell viability was assessed by ALAMARBLUE®, a fluorometric/colorimetric indicator, as previously described.

In Vivo Effect of Mutated RLI on NK and T-Reg Populations.

PBS or mutated RLI were injected every day for 3 days (2 ug per injection). Mice were sacrificed one day later. Spleen and bone marrow were collected, and cells were isolated. NK cells were identified as NK1.1+ CD3− and T-reg cells were CD3+ CD4+ CD25+ FoxP3+, by flow cytometry.

Results

In order to inhibit IL-15 acting through trans-presentation, we have generated a fusion molecule that binds to CD122 with a higher infinity that IL-15 alone (RLI), and mutated at the CD132 interface ($RLI_{Q108D}$). In consequence, the mutated RLI binds efficiently CD122 chain but is unable to transduce a signal within responding cells. We observed that Kit-225, TF-1b and NK-92 cells proliferate in response to both wild-type IL-15 and RLI, whereas no proliferation signal was detected in response to the mutated RLI (FIG. 1). Then, we tested whether the mutated RLI was able to inhibit wild-type RLI-dependent proliferation that directly targets CD122/CD132 dimeric receptor. We found that the mutated RLI efficiently inhibits RLI-dependent cell proliferation, reaching a IC50 at 2 nM (FIG. 2). Surprisingly, we observed that the mutated RLI efficiently abrogated IL-15-dependent proliferation (FIG. 3), whereas no inhibition was observed on IL-2-dependent proliferation (FIG. 4). We found that the mutated RLI was able to inhibit IL-2 dependent signal only when CD25 was blocked (33B3.1 blocking Ab) (FIG. 5). To confirm the potency of the mutated RLI to inhibit IL-15 signal, we assessed a "pulse stimulation" assay by incubating cells with cytokines for 30 min, then after washes to remove unbound cytokine, cells were resuspended in cytokine-free media for 24 h. We observed that the mutated RLI efficiently decreased cell responses to IL-15 and not to IL-2 (FIGS. 7 and 8). Lastly, we investigated whether the mutated RLI could affect NK and T-reg population on mice. For that purpose, we injected the mutated RLI or PBS every day for 3 days (2 ug per injection). One day later, mice were scarified and NK and T-reg were isolated from spleen and bone marrow. We observed that NK population decreased after injection of the mutated RLI in the spleen. Whereas T-regs population remained unchanged. No difference was observed in the bone marrow (FIG. 9).

EXAMPLE 2

Materials and Methods:
Cell Lines

The non-adherent Kit225 human T lymphoma cell line was cultured in RPMI-1640 medium (Gibco-Invitrogen) containing 6% heat-inactivated fetal calf serum, 2 mM glutamine, and 5 ng/mL human rIL-2. The NK-92 cell line, kindly provided by Henri Vié (CRCNA, Nantes, France), was cultured in RPMI-1640 medium (Gibco-Invitrogen) containing 10% heat-inactivated human serum, 2 mM glutamine, and 5 ng/mL human rIL-2. The non-adherent TF-1B human erythroleukemia cell line was cultured in RPMI 1640 medium containing 10% heat inactivated fetal calf serum, 2 mM glutamine, 1 ng/mL GM-CSF and 250 µg/mL geneticin.

Healthy donor blood samples were collected from the French blood bank (Etablissement Francais du Sang (EFS)). Peripheral Blood Mononuclear Cells (PBMC) were isolated on a Ficoll gradient. All cell lines were maintained at 37° C., in a humidified, 5% CO2 atmosphere.

Surface Plasmonic Resonance Studies

The SPR experiments were performed with a BIA-CORE® 3000 biosensor (BIACORE®, Uppsala, Sweden). Recombinant proteins (hCD122, hCD132. Fc-IL-15R.alpha.) were covalently linked to C1\45 sensor chips, and the binding of increasing concentrations of ligands (IL-15, IL-15.sub.Q108D, RLI, RLI.sub.Q108D, RLI.sub.N65K) was monitored. Analysis of sensorgrams was performed using BIAlogue kinetics evaluation software.

Alpha Screen SureFire Assay

Kit225 cells were starved for 12 h in a serum-free medium without IL-2 and plated in 96-well plates at a density of 210.sup.5 cells/well. Kit225 cells were incubated with RLI.sub.Q108D for 30 minutes then stimulated with 40 pM of IL-15 or IL-2 for 1 h. Stat5 phosphorylation was measured using the p-Stat5 Alphascreen Surefire kit (PerkinElmer Life Sciences). After stimulation, cells were lysed. Then, 4.mu.l of lysates were transferred to a 384-well white OPTIPLATE®, a microplate (PerkinElmer Life Sciences), and Stat5 phosphorylation was measured according to the manufacturer's instructions. Stat5 phosphorylation values obtained from untreated condition were subtracted from values obtained in presence of ligands for specific Stat5 phosphorylation values.

Proliferation Assay

The proliferative responses of Kit225 cells to cytokine were quantified by ALAMARBLUE® assay, a fluorometric/colorimetric growth assay (AbD serotec, Kidlington, UK). Briefly, cells were starved in a cytokine-free culture medium overnight for Kit225 cells. Cells were plated at 10.sup.4 cells in 100.mu.l and cultured for 72 hrs in medium supplemented with a fixed concentration of human rIL-15, human rIL-2 or RLI and increasing concentrations of RLI.sub.Q108D antagonist. Cells were pulsed for 6 hrs with 10.mu.L per well of ALAMARBLUE®, a fluorometric/colorimetric indicator. Cell proliferation was assessed by measuring fluorescence at 550/590 nm using Enspire plate reader (Perkin Elmer, Hopkinton Mass., USA).

Flow Cytometry Cell surface expression of h/mCD3, h/mCD8, h/mCD4, h/mNKp46, mNK1.1, mCD27, mCD11b, mCD44, h/mCD132, mCD122, h/mCD25, hIL-15Rα was performed using commercial antibodies. Before staining, Fc receptors were blocked for 15 min at 4° C. with PBS 1% human sera. Cells were incubated for 30 min at 4° C. with antibodies for cell surface staining. Analyses of Stat5 and Stat3 phosphorylations were performed following the protocol of the manufacturer using Lyse/Fix Buffer and Perm Buffer III (BD Biosciences). FoxP3 staining was performed following the protocol outlined in the Foxp3 kit (eBioscience). Samples were acquired on an 8-colors FACS Canto II cytometer (BD bioscience). Analyses were performed using FlowJo software 9.9 (Beckman Coulter).

To study the inhibition of IL-15 trans-presentation by $RLI_{Q108D}$, IL-15Rα stably transfected HeLa cell lines were incubated with IL-15 for 1 hour at 37° C., to allow IL-15 to bind to IL-15Rα and were washed to remove soluble IL-15. Starved Kit225 were incubated with $RLI_{Q108D}$ for 1 h and then cocultured with presenting HeLa cells during 1 hour. The cells were fixed and permeabilized for intracellular p-Stat5 expression analysis.

For Proliferation assay of human PBMC, cells were isolated on a Ficoll gradient. Then, cells were washed in PBS and 1010.sup.6 PBMC were incubated for 10 min at 37.degree. C. with a 1 M final concentration of BD HORIZON™ Dye 450 polymer dye (VPD-450, BD Biosciences). Reaction was stopped by 10-fold dilution with PBS and cells were washed in complete medium R10 (RPMI 1640 medium supplemented with 1 mM sodium/pyruvate, 1 mM non essential amino acids, 100 IU/mL penicillin/streptomycin, 2 mM L-Glutamine and 10% FBS). PBMC were seeded in a 96-well round bottom plate at 110.sup.6 cells/mL in complete medium R10 and incubated at 37.degree. C. at indicated concentrations of cytokines and variants.

In Vivo Models

C57BL/6, Balb/c, and DBA/2 mice were purchased from the Janvier Laboratory. All mice were usually used between the age of 6 and 12 weeks. All animal experiments were approved by the Regional Ethics Committee in Animal experimentation (Pays de la Loire, France) and performed according to European Union Guidelines (authorization number no. B44-278).

For in vivo Stat5 phosphorylation assay, 10 µg of $RLI_{Q108D}$ or PBS were administrated i.p. to C57BL/6 mice, 30 min prior from another 30 min i.p. stimulation with 2 µg of IL-2. Mice were sacrificed and subsequently isolated splenocytes were fixed. Cell suspensions from spleen were prepared by mechanical dilacerations followed by staining for phenotypic analysis. Membrane NKp46 and CD8 staining were performed before cell permeabilization and intracellular p-Stat5 staining.

For poly(I:C) activation, mice were pretreated or not overnight with 10 μg of $RLI_{Q108D}$. Then, mice were activated with 25 μg poly(I:C) together or not with 10 μg of $RLI_{Q108D}$ and studied for NK and CD8 T cell activation in the blood. Surface CD69 expression and intracellular IFNγ after 6 h were analyzed by flow cytometry.

Transplants experiments were performed using sex-matched animals. Mice were anesthetized with a mixture of 75 mg/kg of ketamine and 15 mg/kg of xylazine. The skin transplantation was performed on the right lateral flank of DBA/2 (H-$2^d$) recipient mice with a full-thickness tail skin of Balb/c (H-$2^d$) donor mice. The skin graft was secured with an adhesive bandage for the initial 5 days. Mice were divided into two groups: untreated and $RLI_{Q108D}$-treated groups. Mice were treated with daily intraperitoneal dose (10 μg/mouse) of $RLI_{Q108D}$. Graft survival was then followed by daily visual inspection. All treatments were started on day before the day of skin graft. Rejection was defined as a loss of >80% of the transplanted skin tissue.

Results:

$RLI_{Q108D}$: An IL-15.IL-15Rα Fusion Molecule with Increased Affinity for CD122 and Impaired Recruitment of CD132.

In order to inhibit IL-2 and IL-15 dependent effector functions, we developed an original approach targeting the CD122/CD132 dimer, by combining an increased affinity for CD122 and an impaired recruitment of CD132. On one hand, we found that the low affinity of IL-15 for soluble CD122 (Kd=25 nM) (FIG. 11A) was increased by 14-fold when IL-15 was covalently linked to IL-15Rα (RLI fusion molecule). On the other hand, the mutation of Q108 residue to D on IL-15 has been shown to abrogate its binding to the CD132 chain. This mutation does not affect IL-15/IL-15Rα complex formation, as an IL-$15_{Q108D}$ mutein bound immobilized Fc-IL-15Rα with a similar affinity as wild-type IL-15 (FIG. 11B). We have thus generated $RLI_{Q108D}$, a fusion molecule between IL-$15_{Q108D}$ mutein covalently linked to the soluble IL-15Rα sushi domain. As a control, $RLI_{N65K}$ was produced in which CD122 recruitment was abrogated by introducing the N65K mutation in the IL-15 moiety. Surface Plasmonic Resonance analyses showed, as expected, that $RLI_{Q108D}$ retained a similar affinity for CD122 chain as wild-type RLI (FIGS. 11A and 11C), whereas no binding to immobilized Fc-IL-15Rα was observed (FIG. 11D). By contrast, $RLI_{N65K}$ was unable to bind CD122 (FIG. 11C). Furthermore, soluble CD132 binding to RLI/CD122 complex was completely abrogated when introducing in RLI the Q108D substitution ($RLI_{Q108D}$) (FIG. 11E). In the context of cell membrane-anchored receptors (using Kit-225 and NK-92 cells expressing CD122, CD132, IL-15Rα and IL-2Rα (CD25)), the binding of TU-27 (an anti-CD122 mAb that blocks the binding of IL-2 and IL-15 to CD122) was significantly inhibited by $RLI_{Q108D}$, whereas $RLI_{N65K}$ had no effect. As a control, the binding of the non-blocking CF-1 anti-CD122 mAb was unaffected by either $RLI_{Q108D}$ or $RLI_{N65K}$ (FIG. 12A). Accordingly, $RLI_{Q108D}$ competed out radio-iodinated wt.RLI binding to CD122/CD132 dimeric receptor on NK-92 cells, with IC50 (20 nM) that was however 10-fold higher than that of wt.RLI (2 nM), due to the absence of recruitment of CD132 (FIG. 12B). Thus, $RLI_{Q108D}$ is an original IL-15 derived molecule that combines an increased affinity for CD122 and an impaired recruitment of CD132.

$RLI_{Q108D}$ Inhibits Both IL-15 and IL-2 Signaling Through their Common CD122/CD132 Dimeric Receptor.

Regarding the biological activity of the molecules, as expected, wt.RLI, by acting through the CD122/CD132 dimer, induced Kit225 and NK-92 proliferations (EC50=50 pM), whereas $RLI_{Q108D}$, $RLI_{N65K}$ and IL-$15_{Q108D}$ were inactive (FIGS. 13A and 13B), confirming the necessity of the recruitment of both CD122 and CD132 chains. As expected from the binding studies, $RLI_{Q108D}$ efficiently inhibited both wt.RLI-induced Stat3 and Stat5 phosphorylations (FIG. 14A), as well as Kit225, NK-92 and TF-1β cell proliferations (FIG. 14B), with an IC50 of 5 nM. No inhibitory activity of $RLI_{N65K}$ was observed (FIGS. 14A and 14B), reinforcing the interest of targeting CD132 recruitment, instead of CD122 recruitment.

Moreover, IL-15 trans-presentation by IL-15Rα transfected Hela cells to CD122/CD132 on Kit225 cells was significantly abrogated by $RLI_{Q108D}$ revealing its potency to inhibit IL-15 signaling even during cell-cell interaction (FIGS. 15A and 15B). By contrast, and most importantly, IL-$15_{Q108D}$ was unable to exert such inhibitory effect (FIG. 15A), highlighting the importance of the increased affinity of $RLI_{Q108D}$ over IL-$15_{Q108D}$ for targeting the CD122/CD132 dimer and exerting an inhibitory action.

To test $RLI_{Q108D}$ efficiency on IL-2 signaling through CD122/CD132 dimeric receptor, we used TF-1β cells that express CD122 and CD132 but not IL-2Rα. $RLI_{Q108D}$ efficiently inhibited IL-2-dependend TF-1β cell proliferation with an IC50 of 3 nM (FIG. 16A). Then, we extended our analysis to human primary cells. VPD-450 labeled PBMCs were stimulated with IL-15 or IL-2 in the presence of $RLI_{Q108D}$. We found that CD8 T cell proliferations in response to IL-15 and IL-2 were both inhibited by $RLI_{Q108D}$ (FIGS. 16B-D).

The inhibitory efficiency of $RLI_{Q108D}$ was further confirmed in vivo. When $RLI_{Q108D}$ was administrated into mice prior to injection of wt.RLI, the level of Stat5 phosphorylation within splenic NK cells and CD8 T cell was found to be reduced as compared to that of NK cells from untreated mice (FIGS. 17A and 17B). Thus, IL-2 and IL-15 signaling through the CD122/CD132 dimeric receptor was efficiently inhibited by $RLI_{Q108D}$ in vitro and in vivo.

IL-2Rα Impairs $RLI_{Q108D}$ Inhibition of IL-2 Signaling Through its IL-2Ra/CD122/CD132 Trimeric Receptor.

To address the question whether IL-2Rα and IL-15Rα chains could impact the blocking effect of $RLI_{Q108D}$, we again took advantage of Kit225, NK-92 and TF-1β cells that respond to exogenous IL-2 and IL-15 through their specific trimeric receptor (IL-2Rα/CD122/CD132 for IL-2 and IL-15Rα/CD122/CD132 for IL-15; cis-presentation). Surprisingly, IL-15-induced, but not IL-2-induced, Stat5 phosphorylation in Kit225 cells was inhibited by $RLI_{Q108D}$ (FIG. 18A). Accordingly, $RLI_{Q108D}$ left IL-2-induced cell proliferation unaffected (FIG. 18B). Interestingly, an inhibitory activity of $RLI_{Q108D}$ on IL-2-induced cell proliferation was revealed when adding an antibody (33B3.1) that blocks IL-2 binding to CD25, suggesting that the presence of IL-2Rα precluded $RLI_{Q108D}$ inhibitory action (FIG. 18C). In both assays, $RLI_{N65K}$ was inactive (FIGS. 18B and 18C).

$RLI_{Q108D}$ inhibited IL-15-induced cell proliferation, with an IC50 of 30 nM, 6-fold higher than that of RLI-induced proliferation. Moreover, we found that blocking IL-15Rα by IL-$15_{Q108D}$ enhanced $RLI_{Q108D}$ inhibitory activity (FIG. 18D). This indicates that $RLI_{Q108D}$ inhibitory activity was slightly impaired in the context of the trimeric receptor, and therefore that the presence of IL-15Rα could affect its inhibitory action.

We extended our analysis to human primary cells. IL-15-induced NK cell proliferation was fully abrogated in the presence of RLI$_{Q108D}$ with an IC50 of 5 nM (FIG. 18E). By contrast, IL-2-induced NK cell proliferation was only partially inhibited by RLI$_{Q108D}$, with a high degree of variability among experiments. However, when the blocking anti-CD25 33B3.1 mAb was added to the culture, IL-2-induced NK cell proliferation by RLI$_{Q108D}$ was fully efficient, with a similar IC50 as for inhibition of IL-15-induced proliferation (FIG. 18F). These results confirm the impairment of RLI$_{Q108D}$ action by IL-2Rα. Accordingly to what observed previously, RLI$_{Q108D}$ inhibited the IL-2-induced proliferation of CD4 CD25− T cells, but not that of CD25 expressing conventional CD4 T cells (FIGS. 18G-I). Taken together, these results indicate that RLI$_{Q108D}$ was less efficient in the context of the trimeric receptor, and therefore that the presence of IL-15Rα can also affect its inhibitory action, although not as dramatically as IL-2Rα.

Inhibition of CD122/CD132 Dimeric Receptor by RLI$_{Q108D}$ Limits Cell Activation and Promotes Tolerance.

IL-15 and IL-15Rα are induced during inflammation. To further describe the potency of RLI$_{Q108D}$ to inhibit inflammation related cell activation, poly(I:C) was administrated to mice. IFNγ expression by NK cells from poly(I:C) stimulated mice was significantly impaired by RLI$_{Q108D}$, without affecting CD69 expression at the cell surface (FIG. 19A). However, CD69 expression was decreased on CD8 and CD4 T cells when RLI$_{Q108D}$ was injected together with poly(I:C) (FIGS. 19B and 19C). Thus, TLR stimulation in vivo requires CD122/CD132 dimeric receptor for supporting NK and T cells activation and is inhibited by RLI$_{Q108D}$.

IL-15R⟨ is broadly expressed independently of CD122 and CD132, whereas IL-2Rα expression is restricted mainly to CD4 regulatory T cells (T-reg) and activated T cells. Accordingly to our observations, enrichment by IL-2 of CD4 T cells in FoxP3+ positive cells from human PBMCs was not affected by RLI$_{Q108D}$ (FIG. 20A). As a net result, RLI$_{Q108D}$ treatment shifted the T-reg over CD8 T cell ratio in favor of T-regs (FIG. 20B), highlighting its potential in the promotion of tolerance.

In order to evaluate RLI$_{Q108D}$ efficiency in vivo, RLI$_{Q108D}$ was administered in mice together with IL-2. As expected, IL-2 injection led to an increase of CD44+ CD8 T and NK cells that was completely abrogated by RLI$_{Q108D}$ (FIGS. 20C and 20D). Moreover, by studying NK cell maturation, we found that the CD11b+ CD27− mature NK cell population was dramatically decreased (FIG. 20E). Interestingly, the CD4 T-reg population was not inhibited but even promoted by RLI$_{Q108D}$ when injected together with IL-2 (FIG. 20F), leading to a balance in favor to T-reg cells over NK cells in wild-type mice (FIG. 20G), confirming the results obtained with human PBMCs. Interestingly, high amount of T-reg cells were found within aged mice, and injection of RLI$_{Q108D}$ by itself significantly enhanced splenic T-reg population (FIG. 21A).

Regulatory T cells could prevent allogeneic graft rejection by inhibiting T cell activation. Thus, we wondered whether RLI$_{Q108D}$, that favors by it-self tolerance over cell activation, could present a potential therapeutical benefit using a transplantation model in which skin from Balb/c mice was grafted to DBA/2 recipient. We found that all untreated mice rejected the allogeneic skin graft by day 14. However, a daily treatment with RLI$_{Q108D}$ post-graft resulted in an increase of graft survival (FIG. 21B), supporting the idea that RLI$_{Q108D}$ could favor tolerance.

SEQUENCES:

SEQ ID NO: 1
ITCPPPMSVEHADIWVKSYSLYSRERYICNSGFKRKAGTSSLTECVLNK
ATNVAHWTTPSLKCIRDPALVHQRPAPP

SEQ ID NO: 2
SGGSGGGGSGGGSGGGGSLQ

SEQ ID NO: 3
SGGSGGGGSGGGSGGGGSGG

SEQ ID NO: 4
NWVNVISDLKKIEDLIQSMHIDATLYTESDVHPSCKVTAMKCFLLELQVI
SLESGDASIHDTVENLIILANNSLSSNGNVTESGCKECEELEEKNIKEFL
QSFVHIVQMFINTS

SEQ ID NO: 5
ITCPPPMSVEHADIWVKSYSLYSRERYICNSGFKRKAGTSSLTECVLNKA
TNVAHWTTPSLKCIRDPALVHQRPAPPSGGSGGGGSGGGSGGGGSGGNWV
NVISDLKKIEDLIQSMHIDATLYTESDVHPSCKVTAMKCFLLELQVISLE
SGDASIHDTVENLIILANNSLSSNGNVTESGCKECEELEEKNIKEFLQSF
VHIV<u>D</u>MFINTS

SEQ ID NO: 6
ITCPPPMSVEHADIWVKSYSLYSRERYICNSGFKRKAGTSSLTECVLNKA
TNVAHWTTPSLKCIRDPALVHQRPAPPSGGSGGGGSGGGSGGGGSGGNWV
NVISDLKKIEDLIQSMHIDATLYTESDVHPSCKVTAMKCFLLELQVISLE
SGDASIHDTVENLIILANNSLSSNGNVTESGCKECEELEEKNIKEFL<u>D</u>SF
VHIV<u>D</u>MFINTS

REFERENCES

Throughout this application, various references describe the state of the art to which this invention pertains. The disclosures of these references are hereby incorporated by reference into the present disclosure.

The invention claimed is:

1. A polypeptide comprising the polypeptide of SEQ ID NO:5 or SEQ ID NO:6, having
   an IL15-Ralpha sushi-containing polypeptide,
   a linker, and
   an IL-15 polypeptide wherein the residue at position 108 in the IL-15 polypeptide is not a glutamine (Q).

2. The polypeptide of claim 1, which is fused to an immunoglobulin domain.

3. The polypeptide of claim 2, wherein the immunoglobulin domain is an immunoglobulin constant domain (Fc region).

4. A pharmaceutical composition comprising the polypeptide of claim 1.

* * * * *